「United States Patent [19]
Hamper et al.

[11] Patent Number: 5,969,153
[45] Date of Patent: Oct. 19, 1999

[54] PREPARATION OF SUBSTITUTED 3-ARYL-5-HALOALKYL-PYRAZOLES HAVING HERBICIDAL ACTIVITY

[75] Inventors: Bruce C. Hamper, Kirkwood; Michael K. Mao, Chesterfield, both of Mo.

[73] Assignee: Monsanto Company, St. Louis, Mo.

[21] Appl. No.: 08/943,648

[22] Filed: Oct. 3, 1997

Related U.S. Application Data

[62] Division of application No. 08/667,103, Jun. 20, 1996, Pat. No. 5,698,708.

[51] Int. Cl.$^6$ .................................................. C07D 231/12
[52] U.S. Cl. ............................................ 548/377.1
[58] Field of Search .......................................... 548/377.1

[56] References Cited

U.S. PATENT DOCUMENTS

| | | |
|---|---|---|
| 2,578,654 | 12/1951 | Hearne et al. . |
| 2,695,318 | 11/1954 | Thiele ........................................ 260/61 |
| 2,937,209 | 5/1960 | Studer et al. ............................. 260/649 |
| 3,326,662 | 6/1967 | Tomoyoshi et al. ........................ 71/2.5 |
| 3,395,125 | 7/1968 | Moyer ....................................... 260/67 |
| 3,426,035 | 2/1969 | Bremmer . |
| 3,660,411 | 5/1972 | Levy et al. ........................... 260/293.81 |
| 3,733,321 | 5/1973 | Krapcho . |
| 3,832,403 | 8/1974 | Farona et al. ............................. 260/592 |
| 3,948,937 | 4/1976 | Johnson et al. ........................... 260/311 |
| 4,008,249 | 2/1977 | Fischer et al. ....................... 260/310 R |
| 4,033,986 | 7/1977 | Castenson et al. ................... 260/345.2 |
| 4,052,459 | 10/1977 | Malfroid ................................... 260/592 |
| 4,065,502 | 12/1977 | MacKay et al. .......................... 260/590 |
| 4,072,498 | 2/1978 | Moon et al. ................................. 71/92 |
| 4,096,184 | 6/1978 | Nakamura et al. . |
| 4,160,108 | 7/1979 | Shigeyasu et al. ....................... 562/416 |
| 4,229,466 | 10/1980 | Cardarelli . |
| 4,260,775 | 4/1981 | Plath et al. ............................... 548/362 |
| 4,323,692 | 4/1982 | Tanger ....................................... 560/65 |
| 4,327,104 | 4/1982 | Timmber et al. . |
| 4,329,342 | 5/1982 | Heeres et al. . |
| 4,339,599 | 7/1982 | Jongsma ................................... 562/412 |
| 4,439,620 | 3/1984 | Klauke et al. . |
| 4,485,254 | 11/1984 | Tanger ....................................... 560/21 |
| 4,752,326 | 6/1988 | Ohyama et al. ............................ 71/92 |
| 4,820,845 | 4/1989 | Beck et al. ............................... 548/378 |
| 4,895,984 | 1/1990 | Eggersdorfer et al. ................. 568/319 |
| 5,015,777 | 5/1991 | Chisolm et al. ........................ 568/314 |
| 5,032,165 | 7/1991 | Miura et al. ................................. 71/92 |
| 5,045,106 | 9/1991 | Moedritzer et al. ........................ 71/92 |
| 5,053,517 | 10/1991 | Takigawa et al. ....................... 548/376 |
| 5,068,449 | 11/1991 | Kumai et al. . |
| 5,080,710 | 1/1992 | Rueb et al. . |
| 5,093,529 | 3/1992 | Schmand . |
| 5,108,483 | 4/1992 | Kunisch et al. . |
| 5,112,384 | 5/1992 | Miura et al. . |
| 5,126,489 | 6/1992 | Kurek ....................................... 568/319 |
| 5,146,002 | 9/1992 | Yamada et al. . |
| 5,155,258 | 10/1992 | Kamiya et al. .......................... 562/429 |
| 5,156,668 | 10/1992 | Enomoto et al. . |
| 5,281,571 | 1/1994 | Woodard et al. ..................... 548/377.1 |
| 5,344,992 | 9/1994 | Drews et al. ............................. 568/314 |
| 5,347,054 | 9/1994 | Billeb et al. . |
| 5,468,871 | 11/1995 | Ebel et al. ............................ 548/373.1 |
| 5,489,571 | 2/1996 | Woodard et al. ....................... 504/280 |

(List continued on next page.)

FOREIGN PATENT DOCUMENTS

| | | |
|---|---|---|
| 0344055 | 3/1989 | Australia . |
| 0 020 964 A1 | 1/1981 | European Pat. Off. . |
| 0 116 323 A1 | 8/1984 | European Pat. Off. . |
| 0 317 275 A2 | 5/1989 | European Pat. Off. . |
| 0 361 114 | 4/1990 | European Pat. Off. . |
| 0 443 059 | 8/1991 | European Pat. Off. . |
| 0 619 946 | 10/1994 | European Pat. Off. . |
| 1 330 953 | 5/1963 | France . |
| 55-83751 | 12/1978 | Japan . |
| 62-77370 | 4/1987 | Japan .............................. A01N 43/56 |
| 2-300173 | 9/1988 | Japan . |
| 3-72460 | 5/1989 | Japan . |
| 3-93774 | 9/1989 | Japan . |
| 3-47180 | 2/1991 | Japan .............................. A01N 43/56 |
| 3-81275 | 4/1991 | Japan .............................. A01N 43/60 |
| 3-151367 | 6/1991 | Japan .............................. A01N 43/56 |
| 1147346 | 4/1969 | United Kingdom . |
| WO 90/09975 | 9/1990 | WIPO . |
| WO 92/02509 | 2/1992 | WIPO . |
| WO 92/06962 | 4/1992 | WIPO . |
| WO 94/00407 | 1/1994 | WIPO . |
| WO 95/32188 | 11/1995 | WIPO . |
| WO 96/02486 | 2/1996 | WIPO . |
| WO 96/02515 | 2/1996 | WIPO ......................... C07C 231/16 |

OTHER PUBLICATIONS

Chen, Ted K., et al., "A Convenient Synthesis Of 2,3,5, 6–Tetrahalogenopyridines And Of 3,5–Bis(alkylthio)pyridines From 2,6–Diaminopyridine," *J.C.S. Chem. Comm.*, pp. 1139–1140 (1980).

Fieser, L. F., et al., "Reagents For Organic Synthesis," John Wiley and Sons, Inc., p. 73 (1967).

Gol'dfarb, Ya. L., et al., "New Method For Preparation Of 2–Bromothiophene," *Bulletin of the Academy of Sciences of the USSR Division of Chemical Science*, vol. 31, No. 10(2), pp. 2104–2105 (Oct. 1982).

(List continued on next page.)

*Primary Examiner*—Robert W. Ramsuer
*Attorney, Agent, or Firm*—Grace L. Bonner; Arnold White & Durkee

[57] ABSTRACT

Processes for preparing substituted 3-aryl-5-haloalkyl-pyrazoles and, specifically, for preparing $C_{1-5}$ alkyl esters of 5-[1-($C_{1-5}$ alkyl)-4-halo-5-($C_{1-3}$ haloalkyl)-1H-pyrazole-3-yl]-2,4-dihalo-benzoic acids such as isopropyl 5-[4-bromo-1-methyl-5-(trifluoromethyl)-1H-pyrazole-3-yl]-2-chloro-4-fluorobenzoate, are presented. The described processes include novel approaches for forming phenyl-diketones, forming and alkylating pyrazoles, brominating heterocyclic compounds, oxidizing alkyl-substituted benzene compounds, and esterifying carboxylic acids. These processes may be combined to prepare 3-aryl-5-haloalkyl pyrazoles, or alternatively, used in subcombinations or individually to prepare intermediates or other useful compounds.

14 Claims, No Drawings

U.S. PATENT DOCUMENTS

| | | |
|---|---|---|
| 5,530,126 | 6/1996 | Woodward et al. . |
| 5,532,416 | 7/1996 | Hamper et al. . |
| 5,536,700 | 7/1996 | Woodard et al. . |
| 5,545,609 | 8/1996 | Higashimura et al. . |
| 5,587,485 | 12/1996 | Chupp et al. . |
| 5,600,008 | 2/1997 | Hamper et al. . |
| 5,600,016 | 2/1997 | Hamper et al. . |
| 5,654,490 | 8/1997 | Hamper et al. . |

OTHER PUBLICATIONS

Grimmett, M. Ross, "Halogenation Of Heterocycles: I. Five–Membered Rings," *Advances In Heterocyclic Chemistry,* vol. 57, pp. 291, 293–297, 336, 341–343 (1993).

Houben–Weyl, "Carbonsäuren und Carbonsäure–Derivate," *Methoden der Organischen Chemie,* vol. E5, pp. 677–678 (1985).

Itahara, Toshio, et al., "Chloroperoxidase Catalyzed Halogenation Of Pyrimidine Bases," *Chemistry Letters,* pp. 2311–2312 (1987).

Kellogg, B. A., et al., "Base Catalyzed Hydrolysis And $^{18}O{=}C$ Exchange Of Ethyl And Isopropyl Toluoate In $H_2O$ and $D_2O$ Media. The Anionic Tetrahedral Intermediates Are Protonically Equilibrated," *J. Am. Chem. Soc.,* vol. 117, No. 6, pp. 1731–1735 (1995).

Kivinen, Antti, "Mechanisms Of Substitution At The COX Group," *The Chemistry Of Functional Groups,* pp. 177, 182–191 (1972).

Trujillo, John I., et al., "Facile Esterification Of Sulfonic Acids And Carboxylic Acids With Triethylorthoacetate," *Tetrahedron Letters,* vol. 34, No. 46, pp. 7355–7358 (1993).

Chemical Abstract No. 92:57881s (1980).

Chemical Abstract No. 109:230773c (1988).

Berlengua et al., "Synthesis of Halogenated . . . 4–Chloropyrazoles," *J. Heterocycl. Chem.,* 23(2), pp. 459–461 (1986).

Blackman et al., "Amathamide Alkaloids from the Marine Bryozoan Amatha Wilsoni Kirkpatrick," *Heterocycles,* 85, vol. 23 (11), pp. 2828–2833 (1985).

Broxton et al., "Ring Bromination of Aryl . . . Hypobromous Acid," *J. Chem. Soc.,* Perkin Trans. 1, 74 (15), pp. 1769–1771 (1974).

Burger et al., "1,5–Diazabicyclo[3,3,0]octa–2,6–dien . . . 4,5–Diazaocta–1,3,5,7–tetraen Ein . . . Pyrazol–Synthesen," *Chemische–Berichte,* 112, pp. 2620–2630 (1979).

Chemical Abstract 114:164226b (1991).

Chemical Abstract 199:27827n (1993).

Chemical Abstract 122:265364 (1995).

Friedlaender et al., *Chemische Berichte,* vol. 47, pp. 3040–3052 (1914).

Ishihara et al., "A New Effective . . . F–Alkyl Ketones," *Chem. Letters,* pp. 819–822 (1988).

Joshi et al., "Studies . . . Compounds IV," *J. Inorg. Nucl. Chem.,* 39, pp. 803–810 (1977).

Joshi et al., "Studies . . . Derivatives," *Indian J. Chem.,* 14B, pp. 1004–1006 (1976).

Frank, et al., "A Modified Procedure for Acid–Catalyzed Esterification with Isopropanol," *Chromatographia,* vol. 12, No. 3, pp. 168–170 (Mar. 1979).

Leung, et al., "Metabolism and Distribution of the Experimental Triazolone Herbicide F6285 [1–[2, 4–Dichloro–5–[N–(methylsulfonyl)amino]phenyl]–1, 4–dihydro–3–methyl–4–(difluoromethyl)–5H–triazol–5–one] in the Rat, Goat, and Hen," *J. Agric. Food Chem.,* vol. 39, pp. 1509–1514 (1991).

Morrison, et al., "Organic Chemistry," 5th ed., Ch. 23, p. 824, Allyn and Bacon, Inc., 1959.

Nakatsuka, et al., "Methyl Group at 1–Position of Stabilized Indole as a Protective Group," *Heterocycles,* vol. 24, No. 10, pp. 2791–2792 (1986).

Frick, W. et al., "Critical Experimental Parameters in Gas Chromatographic–Mass Spectrometric Analysis of Oligopeptide Hydrolysates at the Picomole Level" *Analytical Chemsitry__,* vol. 49, No. 8, pp. 1241–1245 (1977).

Brooks et al., "Gas Chromatographic Studies of Catecholamines, Tryptamines, and Other Biological Amines" *Analytical Chemistry,* vol. 36, No. 8, pp. 1540–1545 (1964).

Hartmann et al., "Untersuchungen an Diazoverbindungen Und Arsden–Xx" *Phosphorics,* vol. 5, pp. 21–29 (1974) (abstract only in English).

Katritzky, "Advances in Heterocyclic Chemistry" *Academic Press,* vol. 6, pp. 358–361 (1966).

Aranes et al., "Hydroperoxides as Pseudohalides Oxidatio, Oxidative Alkylation, Acylation, and Arylation of Acrylonitrile", J. Chem. Soc., Chem. Commun., (1995).

F. Texier–Boullet, "Pyrrole & Pyrazole Ring Closure in Heterogeneous Media", Synthesis, pp. 409–411, (1986).

Ingle, "Synthesis of Some New 3,5–Disubstituted–Pyrazoles", J. Indian Chem. Soc., p. 852, (1988).

Joshi et al., "Studies in Fluorinated B–Diketones & Related Compounds", Indian J. of Chem., pp. 485–488, (1972).

Ng. pH Buu–Hoi et al., Carcinogenic Nitrogen Compounds, The Radium Institute, pp. 386–388 (1952).

Araneo et al., "Hydroperoxides as Pseudohalides" J. Chem. Soc., pp. 1399–1400 (1995).

R. Karimi–Khoozani et al., Syntheses of substituted (1–methyl–5–nitro–2–imidazolyl) pyrazles, Issue No. 3, pp. 503–510, (1994).

Chemical Abstracts 122:265037 (1995).

Chemical Abstracts 91:19178 (1979).

Chemical Abstracts WO 8902887A (1989).

Chemical Abstracts 111:115098R, vol. 111, (1989).

Chemical Abstracts 120:244818k, vol. 120, (1994).

Chemical Abstracts 91–105689/15 (1991).

Chemical Abstracts 115:159132, Issue 22, (1991).

Chemical Abstracts 110(11):95234f, (1990).

Chemical Abstracts 1053231, (1979).

Chemical Abstracts 70:114911, (1969).

Chemical Abstacts 119, 71940, (1993).

Chemical Absttact 123:284872 (1995).

Chemical Abstracts 97:72283V (1982).

Chemical Abstracts 97:72285 (1982).

Buu–Hoi, et al., "Carcinogenic Nitrogen Compounds. Part XIV. Friedel–Crafts Reactions with m– and p–Fluorotoluene," *J. Chem. Soc.,* pp. 386–388 (1953).

Gilman, et al., "Metalation of Aryl Fluorides in Tetrahydrofuran," *J. Org. Chem.,* vol. 22, pp. 1715–1716 (1957).

Gross, et al., *Chem. Ber.,* vol. 96, pp. 308–313 (1963).

Joshi, et al., "Studies in Fluorinated β–Diketone & Related Compounds: Part I—Syntheses of Some New Fluorinated β–Diketones & Their Copper Chelates," *Indian J. Chem.,* vol. 10, No. 5, pp. 485–488 (May 1972).

Osman, et al., "Synthesis of Unbranched 4–Alkylbenzalaldehydes," *Helv. Chim. Acta.,* vol. 65, pp. 2448–2449 (1982).

Pathak, et al., "Synthesis and Biological Activities of Some New 2–Arylamino–4–Fluoroarylthiazoles," *Pharmazie,* vol. 36, No. 5, pp. 331–332 (1981).

Rieche, et al., *Chem. Ber.,* vol. 93, pp. 88–94 (1960).
Scarpati, et al., *Synthetic Communications,* vol. 20, No. 17, pp. 2565–2572 (1990).
Sharma, et al., "Synthesis and Antifungal Activity of Aryloxyacetyl Hydrazones of Fluoro Aralkyl/Diaryl Ketones," *J. Indian Chem. Soc.,* vol. 61, No. 7, pp. 644–646 (Jul. 1984).
Shingare, et al., "Synthesis of Some Sulfonamide Derivatives," *J. Indian Chem. Soc.,* vol. 54, No. 7, pp. 705–708 (Jul. 1977).

PREPARATION OF SUBSTITUTED 3-ARYL-5-HALOALKYL-PYRAZOLES HAVING HERBICIDAL ACTIVITY

This is a divisional of application Ser. No. 08/667,103 filed Jun. 20, 1996 now U.S. Pat. No. 5,698,708.

BACKGROUND OF THE INVENTION

The present invention generally relates to the preparation of substituted 3-aryl-5-haloalkyl-pyrazoles having herbicidal activity, and specifically, to novel processes for preparing $C_{1-5}$ alkyl esters of 5-[1-($C_{1-5}$ alkyl)-4-halo-5-($C_{1-3}$ haloalkyl)-1H-pyrazole-3-yl]-2,4-dihalo-benzoic acids such as isopropyl 5-[4-bromo-1-methyl-5-(trifluoromethyl)-1H-pyrazole-3-yl]-2-chloro-4-fluorobenzoate. While the invention is preferably directed to the preparation of such 3-aryl-5-haloalkyl-pyrazoles, the invention also relates to the individual process steps for forming phenyl-diketones, forming and alkylating pyrazoles, brominating pyrazoles and other heterocyclic compounds, oxidizing alkyl-substituted benzene compounds, and esterifying carboxylic acids.

Various substituted aryl-pyrazole compounds are known and used as chemical intermediates, pharmaceuticals and herbicides. Exemplary U.S. Patents include U.S. Pat. No. 3,326,662 to Tomoyoshi et al., U.S. Pat. No. 3,948,937 to Johnson et al., U.S. Pat. No. 4,008,249 to Fischer, deceased et al., U.S. Pat. No. 4,072,498 to Moon et al., U.S. Pat. No. 4,260,775 to Plath et al., U.S. Pat. No. 4,468,871 to Ebel et al., U.S. Pat. No. 4,752,326 to Ohyama et al., U.S. Pat. No. 5,032,165 to Miura et al., U.S. Pat. No. 5,045,106 to Moedritzer et al. A variety of 3-aryl-5-haloalkyl pyrazoles are disclosed in U.S. Pat. Nos. 5,281,571 and 5,489,571 to Woodard et al.

Processes are generally known for making aryl-pyrazole compounds. U.S. Pat. No. 5,281,571 to Woodard et al. sets forth a method for preparing substituted 3-aryl-5-haloalkyl-pyrazoles. Briefly, an acetophenone having a methyl substituent on the phenyl moiety is reacted with an ester in the presence of a base to form a phenyl diketone, which is subsequently isolated and then cyclized by treatment with hydrazine. The resulting aryl-pyrazole is subjected to further process steps, including N-alkylation and halogenation of the pyrazole moiety, oxidation of the methyl group on the phenyl moiety to form a benzoic acid, and formation of benzoic acid derivatives thereof.

While methods such as these are suitable for preparing substituted 3-aryl-5-haloalkyl-pyrazoles, the methods are not optimized with regard to minimizing the expense of reagents, maximizing the selectivity of regioisomers, or maximizing product yields and throughput.

SUMMARY OF THE INVENTION

It is therefore an object of the present invention to optimize the process steps for preparing 3-aryl-5-haloalkyl pyrazoles with respect to cost, reliability, selectivity, yield and throughput. It is also an object of the invention to provide improved protocols for bromination of heterocyclic compounds, for oxidation of alkyl-substituted benzene substrates and for esterification of substituted or unsubstituted carboxylic acids.

Briefly, therefore, the present invention is directed to a process for preparing a compound of Formula IIIb

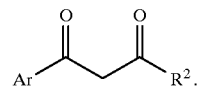

An acetophenone of Formula IIIa

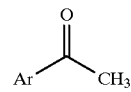

is acylated with a haloacylhalide of Formula A1

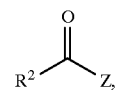

which has a fully halogenated α-carbon. In this process: Ar is phenyl or substituted phenyl, $R^2$ is $C_{1-3}$ haloalkyl, and Z is halogen.

The invention is also directed to a process for preparing a compound of Formula IIId

A phenyl-diketone of Formula IIIb

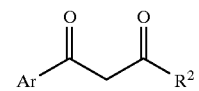

is condensed with hydrazine in a reaction mixture to form an alkyl-pyrazole-precursor intermediate. The hydrazine is present in the reaction mixture in a stoichiometric excess amount relative to the phenyl-diketone. The amount of excess hydrazine is at least about 15 mole percent of the sum of the molar amount of unreacted phenyl-diketone and the molar amount of intermediate formed. Excess hydrazine is then removed from the reaction mixture, and the intermediate is alkylated with an alkylating agent. In this process: Ar is phenyl or substituted phenyl; $R^1$ is alkyl or alkyl substituted with halogen, amino, nitro, cyano, hydroxy, carboxy, alkoxy, thio, mercaptoalkyl or alkylthio; and $R^2$ is alkyl, hydroxy, alkoxy, acyl, carboxylic acid and aldehyde, amide and ester derivatives thereof, halogen, haloalkyl, amino, nitro, cyano, mercaptoalkyl, alkylthio, alkylsulfinyl, alkylsulfonyl, alkylphosphinyl or alkylphosphonyl.

In another process for preparing a compound of Formula IIId, a phenyl-diketone of Formula IIIb is condensed with hydrazine in a reaction mixture to form an alkyl-pyrazole-precursor intermediate. Hydrazine is present in the reaction mixture in a stoichiometric excess amount relative to the phenyl-diketone. The reaction mixture has an organic phase and an aqueous phase, and hydrazine is removed from the reaction mixture by removing the aqueous phase from the reaction mixture. The intermediate is then alkylated with an alkylating agent. Ar, $R^1$ and $R^2$ are defined in this process as in the process immediately preceding.

The invention is directed as well to a process for preparing an alkylated pyrazole compound of Formula IIIe

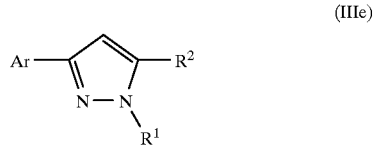
(IIIe)

comprising condensing a phenyl-diketone of Formula IIIb with hydrazine in a reaction mixture to form an alkyl-pyrazole-precursor intermediate. The intermediate is alkylated under acidic conditions with an alkylating agent. Ar, and $R^1$ are defined as in the process immediately preceding. $R^2$ is alkyl, hydroxy, alkoxy, acyl, carboxylic acid and aldehyde, amide and ester derivatives thereof, halogen, haloalkyl, amino, nitro, cyano, mercaptoalkyl, alkylthio, alkylsulfinyl, alkylsulfonyl, alkylphosphinyl or alkylphosphonyl. $R^2$ is preferably an electron withdrawing group and most preferably a haloalkyl.

The invention is additionally directed to a process for regioselectively alkylating a 3(5)-aryl-5(3)-haloalkylpyrazole. A compound of Formula IIIc,

(IIIc)

is alkylated with an alkylating agent without deprotonating the N-hydrogen of the compound of Formula IIIc. The resulting 3-aryl isomer of a 1-alkyl-3(5)-aryl-5(3)-haloalkyl-pyrazole has the Formula IIIe

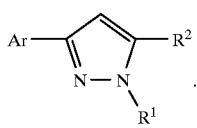
(IIIe)

While the reaction also results in the formation of a corresponding 5-aryl isomer thereof, the amount of 3-aryl isomer formed is at least about 90% of the total amount of 1-alkyl-3(5)-aryl-5(3)-haloalkyl-pyrazole formed. In this process: Ar is phenyl or substituted phenyl; $R^1$ is $C_{1-5}$ alkyl; and $R^2$ is $C_{1-3}$ haloalkyl.

The invention is directed, moreover, to a process for brominating a heterocyclic substrate. The heterocyclic substrate is reacted with a bromide salt under oxidizing conditions.

The invention is further directed to a process for directly oxidizing an alkyl-substituted benzene substrate. The substrate is reacted with molecular oxygen in the presence of metal salt catalyst and benzoyl peroxide.

The invention is directed to processes for esterifying a carboxylic acid substrate. In a first esterification protocol, the carboxylic acid is reacted with a halogenating agent, and the resulting acid halide is esterified to form the corresponding carboxylic acid ester. The esterification reagent used in this process is formed by mixing an alcohol and an acylhalide. In a second, and independent esterification protocol, a carboxylic acid substrate is esterified with a trialkylorthoester of Formula F1

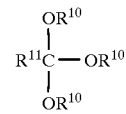
(F1)

to form a carboxylic acid ester. In this process, $R^{10}$ is $C_{3-5}$ alkyl and $R^{11}$ is hydrogen or alkyl.

The present invention is also directed to processes for preparing a compound of Formula I

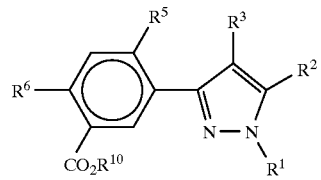
(I)

A compound of Formula If

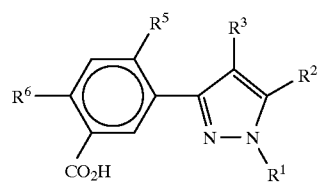
(If)

is halogenated to form an acid halide and the acid halide is then esterified with an esterification reagent. The esterification reagent is formed by mixing an alcohol of Formula $R^{10}OH$ and an acylhalide. In this process: $R^1$ is $C_{1-5}$ alkyl; $R^2$ is $C_{1-3}$ haloalkyl; $R^3$, $R^5$ and $R^6$ are halogen; and $R^{10}$ is $C_{3-5}$ alkyl.

In another process for preparing a compound of Formula I, a compound of Formula If

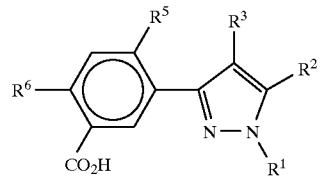
(If)

is esterified with a trialkylorthoester of Formula F1

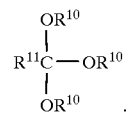
(F1)

$R^1$, $R^2$, $R^3$, $R^5$, $R^6$ and $R^{10}$ are defined as in the immediately preceding process and $R^{11}$ is hydrogen or alkyl.

In an additional process for preparing a compound of Formula I, a compound of Formula Ie

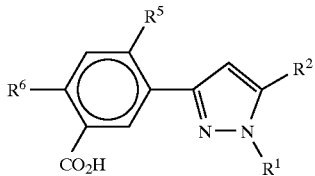

(Ie)

is brominated with a bromide salt under oxidizing conditions to form a compound of Formula If and the compound of Formula If is esterified. In this process: $R^1$, $R^2$, $R^5$, $R^6$ and $R^{10}$ are defined as in the immediately preceding process and $R^3$ is bromo.

In a further process for preparing a compound of Formula I, a compound of Formula Id

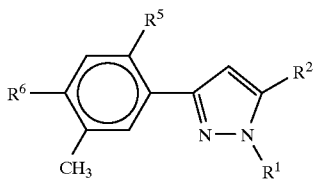

(Id)

is oxidized with molecular oxygen in the presence of metal salt catalyst, catalyst promoter and benzoyl peroxide to form a compound of Formula Ie

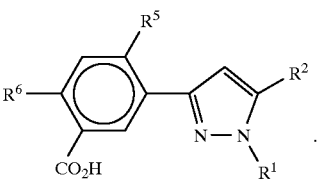

(Ie)

The compound of Formula Ie is then halogenated to form a compound of Formula If, which is itself subsequently esterified. $R^1$, $R^2$ $R^5$, $R^6$ and $R^{10}$ are as defined in the immediately preceding process. $R^3$ is halogen.

In still another process for preparing compounds of Formula I, a compound of Formula Ib

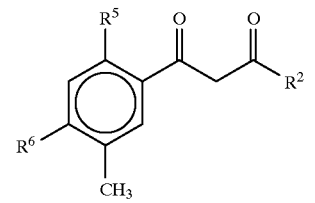

(Ib)

is condensed with hydrazine in a reaction mixture to form an alkyl-pyrazole-precursor intermediate. The intermediate is then alkylated with an alkylating agent under acidic conditions to form a compound of Formula Id,

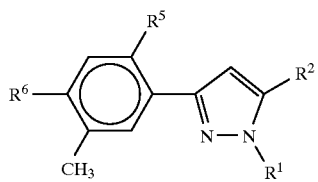

(Id)

The compound of Formula Id is then oxidized to form a compound of Formula Ie, which is subsequently halogenated to form a compound of Formula If, which is subsequently esterified. In this process, $R^1$, $R^2$, $R^3$, $R^5$, $R^6$ and $R^{10}$ are defined as in the immediately preceding process.

In an additional process for forming a compound of Formula I, a compound of Formula Ia

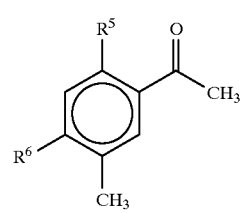

(Ia)

is acylated with a haloacylhalide having a fully halogenated α-carbon and represented structurally as Formula A1

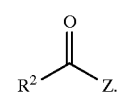

(A1)

The resulting compound of Formula Ib is condensed with hydrazine to form an alkyl-pyrazole-precursor intermediate. The intermediate is alkylated with an alkylating agent to form a compound of Formula Id, which is oxidized to form a compound of Formula Ie, which is halogenated to form a compound of Formula If, which is esterified to form a compound of Formula I. In this process, $R^1$, $R^2$, $R^3$, $R^5$, $R^6$ and $R^{10}$ are defined as in the process immediately preceding.

In still a further process for preparing a compound of Formula I, a compound of Formula Ia is acylated with a haloacetylhalide or an alkyl haloacetate to form a phenyl diketone of Formula Ib. The phenyl-diketone is condensed with hydrazine in a reaction mixture to form an alkyl-pyrazole-precursor intermediate. The reaction mixture has an organic phase and an aqueous phase, and hydrazine is present in the reaction mixture in a stoichiometric excess amount relative to the compound of Formula Ib. The reaction mixture is heated to dissolve into the organic phase any amount of precipitate which may have formed and to separate the aqueous phase from the organic phase. Excess hydrazine is then removed from the reaction mixture by removing the aqueous phase from the reaction mixture. The intermediate is alkylated with an alkylating agent under acidic conditions to form a compound of Formula Id, which is subsequently oxidized with molecular oxygen in the presence of metal salt catalyst, halide salt and acetone promoter and benzoyl peroxide to form a compound of Formula Ie, which is then halogenated to form a compound of Formula If, which is then esterified to form a compound of Formula I. In this process, $R^1$, $R^2$, $R^3$, $R^5$, $R^6$ and $R^{10}$ are as defined for the immediately preceding process.

The present invention is further directed to a process for preparing a compound of Formula II

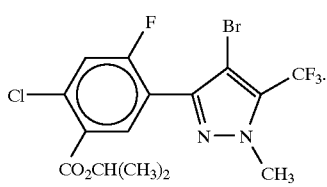
(II)

In this process, a compound of Formula IIa

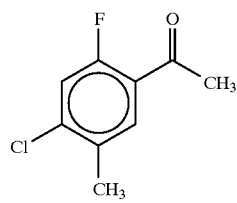
(IIa)

is acylated with trifluoroacetylhalide or ethyl trifluoroacetate to form a compound of Formula IIb,

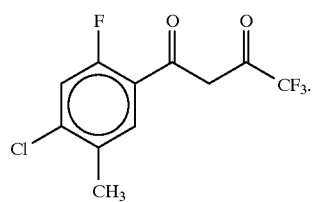
(IIb)

The compound of Formula IIb is then condensed with hydrazine in a reaction mixture to form an alkyl-pyrazole-precursor intermediate. Hydrazine is present in the reaction mixture in a stoichiometric excess amount relative to the compound of Formula Ib. The reaction mixture, which has an organic phase and an aqueous phase, is then heated to dissolve into the organic phase any amount of precipitate which may have formed. Such heating also facilitates separation of the aqueous phase from the organic phase layers. Excess hydrazine is removed from the reaction mixture by removing the aqueous phase. The intermediate is then alkylated with a methylating agent under acidic conditions to form a compound of Formula IId,

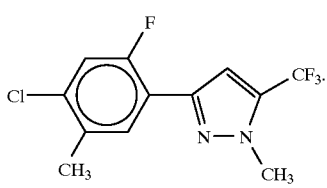
(IId)

The compound of Formula IId is oxidized with molecular oxygen in the presence of metal salt catalyst, halide salt, acetone and benzoyl peroxide to form a compound of Formula IIe,

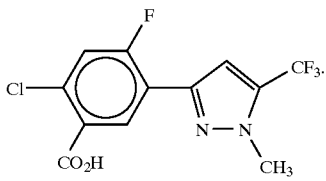
(IIe)

The compound of Formula IIe is brominated with a bromide salt under oxidizing conditions to form a compound of Formula IIf

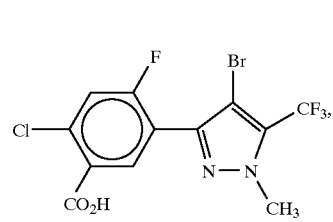
(IIf)

which is then esterified to form a compound of Formula II.

Other features and objects of the present invention will be in part apparent to those skilled in the art and in part pointed out hereinafter.

DETAILED DESCRIPTION OF THE INVENTION

The present invention includes novel process steps for forming phenyl-diketones, forming and alkylating pyrazoles, brominating pyrazoles and other heterocyclic compounds, oxidizing alkyl-substituted benzene compounds, and esterifying carboxylic acids. These steps may be combined to prepare 3-aryl-5-haloalkyl pyrazoles, or alternatively, used in subcombinations or individually to prepare intermediates or other compounds. The bromination, oxidation and esterification processes presented herein are particularly suited to a broader range of substrates, as detailed below. The methods presented herein confer significant advantages over the prior art methods in terms of cost, reliability, selectivity, yield and throughput. Specific advantages for particular process steps are discussed below.

The 3-aryl-5-haloalkyl pyrazoles prepared by the methods of the present invention may be used to provide outstanding control of broadleaf and narrowleaf weeds such as gallium, blackgrass, pigweed, cocklebur, velvetleaf and hemp sesbania in various crops such as corn, soybean, wheat, barley, rice and nuts. They are also effective in forestry against undesirable trees and vines. The 3-aryl-5-haloalkyl pyrazoles may be applied in a variety of application modes and may be used as herbicidal compositions, as co-herbicides, or in combination with safeners, fungicides, insecticides, nematicides and/or other disease control agents. The herbicidal compound prepared according to the preferred embodiment of the invention, isopropyl 5-[4-bromo-1-methyl-5-(trifluoromethyl)-1H-pyrazole-3-yl]-2-chloro-4-fluorobenzoate, is especially effective for preemergent control of broadleaf and narrowleaf weeds associated with small-grain crops such as wheat.

As used herein, the terms "alkyl", "alkenyl", or "alkynyl", whether used alone or in compound form (e.g., haloalkyl, alkoxy, alkoxyalkyl, etc.), refers to both linear and/or branched-chain moieties. Representative, non-limiting alkyl, alkenyl, alkynyl, cycloalkyl, cycloalkylalkyl, cycloalkenyl and cycloalkenylalkyl members include the following: methyl, ethyl, the isomeric propyls, butyls, pentyls, hexyls, heptyls, octyls, nonyls, decyls, etc.; vinyl, allyl, crotyl, methallyl, the isomeric butenyls, pentenyls, hexenyls, heptenyls, octenyls; ethynyl, the isomeric propynyls, butynyls, pentynyls, hexynyls, etc.; the alkoxy, polyalkoxy, alkoxyalkyl and polyalkoxyalkyl analogs of the foregoing alkyl groups, e.g., methoxy, ethoxy, propoxys, butoxys, pentoxys and hexoxys and corresponding polyalkoxys and alkoxyalkyls, e.g., methoxymethoxy, methoxyethoxy, ethoxymethoxy, ethoxyethoxy, methoxymethyl, methoxyethyl, ethoxymethyl, ethoxyethyl, propoxymethyl, isopropoxymethyl, butoxymethyl, isobutoxymethyl, tertbutoxymethyl, pentoxymethyl, hexoxymethyl, etc., cyclopropyl, cyclobutyl, cyclopentyl, cyclohexyl, cycloheptyl, cyclopropylmethyl, cyclobutylmethyl, cyclopentylmethyl, etc.; the isomeric cyclopentenes, cyclohexenes and cycloheptenes having mono- or di-unsaturation; representative aryl, aralkyl and alkaryl groups include phenyl, the isomeric tolyls and xylyls, benzyl, naphthyl, etc.

The term "haloalkyl" refers to alkyl radicals substituted with one or more halogen (chloro, fluoro, bromo or iodo) atoms. Polyhaloalkyl members may have the same or mixed types of halogen atoms. A "perhaloalkyl" refers to an alkyl in which each of the hydrogen atoms is substituted with halogen atoms. A haloalkyl which is "fully halogenated" at a particular carbon atom has halogen atoms in place of all the hydrogen atoms normally bonded to that carbon. Representative mono-, di- and tri-haloalkyl members include: chloromethyl, chloroethyl, bromomethyl, bromoethyl, iodomethyl, iodoethyl, chloropropyl, bromopropyl, iodopropyl, 1,1,-dichloromethyl, 1,1dibromomethyl, 1,1-dichloropropyl, 1,2-dibromopropyl, 2,3-dibromopropyl, 1-chloro-2-bromoethyl, 2-chloro-3-bromopropyl, trifluoromethyl, trichloromethyl, etc.

The term "heterocyclic" as used herein refers to a closed-ring structure in which one or more of the atoms in the ring is other than carbon. Exemplary heterocyclic members include: alkylthiodiazolyl; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyanothienyl; thienylalkyl; alkyl-substituted thienyl; 4,5-polyalkylene-thienyl; piperidinyl; alkylpiperidinyl; pyridyl; di- or tetrahydropyridinyl; alkyltetrahydromorpholyl; alkylmorpholyl; azabicyclononyl; diazabicycloalkanyl, benzoalkylpyrrolidinyl; oxazolidinyl; perhydrooxazolidinyl; alkyloxazolidyl; furyloxazolidinyl, thienyloxazolidinyl, pyridyloxazolidinyl, pyrimidinyloxazolidinyl, benzooxazolidinyl, $C_{3-7}$ spirocycloalkyloxazolidinyl, alkylaminoalkenyl; alkylideneimino; pyrrolidinyl; piperidonyl; perhydroazepinyl; perhydroazocinyl; pyrazolyl; dihydropyrazolyl; piperazinyl; perhydro-1,4-diazepinyl; quinolinyl, isoquinolinyl; di-, tetra- and perhydroquinolyl- or -isoquinolyl; indolyl and di- and perhydroindolyl, etc.

The processes of the present invention are preferably employed to prepare 3-aryl-5-haloalkyl pyrazole compounds of Formula I,

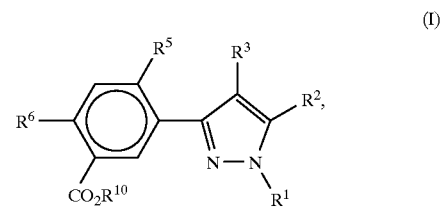

wherein $R^1$ is $C_{1-5}$ alkyl, $R^2$ is $C_{1-3}$ haloalkyl, $R^3$, $R^5$ and $R^6$ are halogen and $R^{10}$ is $C_{1-5}$ alkyl. The haloalkyl $R^2$ is preferably fully halogenated at the carbon nearest the pyrazole ring. In a most preferred embodiment, the processes are used to prepare isopropyl 5-[4-bromo-1-methyl-5-(trifluoromethyl)-1H-pyrazole-3-yl]-2-chloro-4-fluorobenzoate, structurally represented as the compound of Formula II,

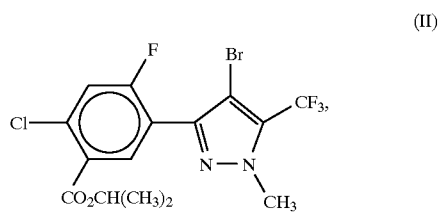

The preparation of the aryl-pyrazole of Formula II is generally set forth as described below for compounds of Formula I, and is further exemplified in Example 1. In the process steps described below, the various symbols defining radical substituents (e.g. $R^1$, $R^2$, etc.) have the same meaning as defined for the compounds of Formula I, unless otherwise indicated.

A preferred overall process for producing compounds of Formula I starts with substituted acetophenones of Formula Ia,

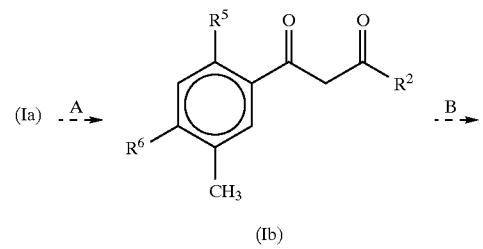

which may be converted to compounds of Formula I through a series of process steps (A through E) which effect the following conversions:

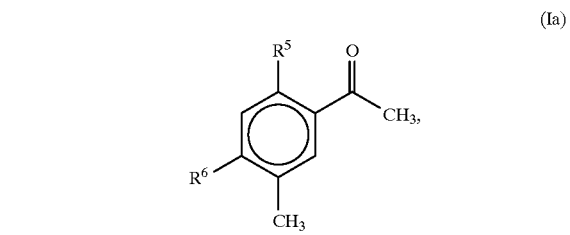

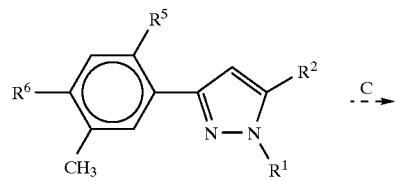

(Id)

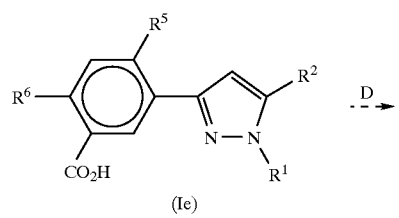

(Ie)

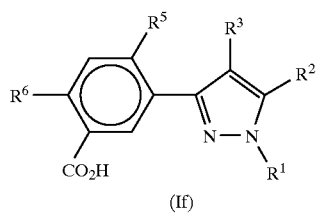

(If)

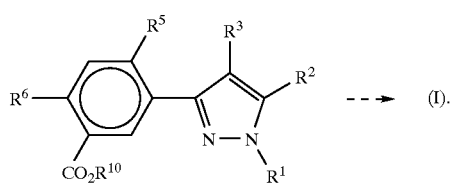

(I).

Process A

Process A relates to the acylation of acetophenones to form phenyl-diketones. While the acetophenones used in the acylation step are, as described below, preferably 2,4-dihalo-5-methyl-acetophenones, the present invention encompasses using acetophenones in which the phenyl moiety is unsubstituted or has other substituents. In the general case, an acetophenone of the Formula IIIa may be converted to a phenyl-diketone of the Formula IIIb according to the reaction:

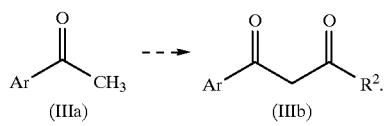

wherein Ar is phenyl or substituted phenyl and $R^2$ is a $C_{1-3}$ haloalkyl and is fully halogenated at the carbon which is nearest the carbonyl once the phenyl-diketone is formed.

As used herein, the term "substituted phenyl" refers to a radical having the Formula Ar-1,

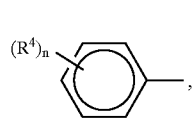

(Ar-1)

wherein $R^4$ is selected from the group consisting of: $C_{1-8}$ alkyl; $C_{3-8}$ cycloalkyl, cycloalkenyl, cycloalkylalkyl or cycloalkenylalkyl; $C_{2-8}$ alkenyl or alkynyl; benzyl; the aforementioned members substituted with halogen, amino, nitro, cyano, hydroxy, alkoxy, alkylthio,

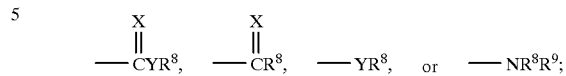

mercaptoalkyl; alkoxyalkyl or polyalkoxyalkyl; carbamyl; amino, nitro or cyano; halogen; hydroxy; $C_{1-10}$ heterocycle containing O, S(O), and/or $NR^8$ heteroatoms; $C_{6-12}$ aryl, aralkyl, or alkaryl;

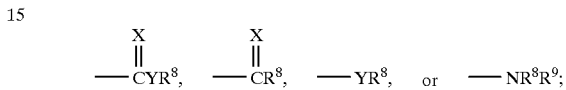

and two or more of the aforementioned $R^4$ members combined through a linking group to form a cyclic ring having up to 9 ring members which may be substituted with any of the $R^4$ members, the linking group including saturated or unsaturated carbon, —(C=X)—, hetero O, hetero $S(O)_m$, and hetero $NR^8$; X is O, $S(O)_m$, $NR^8$, or $CR^8R^9$; Y is O, $S(O)_m$, $NR^8$; m is 0–2; n is 1–5; and $R^8$ and $R^9$ are selected from the group consisting of: hydrogen; $C_{1-8}$ alkyl; $C_{3-8}$ cycloalkyl, cycloalkenyl, cycloalkylalkyl or cycloalkenylalkyl; $C_{2-8}$ alkenyl or alkynyl; benzyl; the aforementioned members substituted with halogen, amino, nitro, cyano, hydroxy, alkoxy, alkylthio; thioalkyl; alkoxyalkyl; polyalkoxyalkyl; carbamyl; halogen; amino; nitro; cyano; hydroxy; $C_{1-10}$ heterocycle containing O, $S(O)_m$ and/or N heteroatoms; $C_{6-12}$ aryl, aralkyl, or alkaryl; and two or more of the aforementioned members combined through a linking group to form a cyclic ring having up to 9 ring members which may be substituted with any of the members, the linking group including saturated or unsaturated carbon, —(C=X)—, hetero O, hetero $S(O)_m$, and hetero N.

The substituted phenyl of the present invention more preferably includes compounds of the Formula Ar-2,

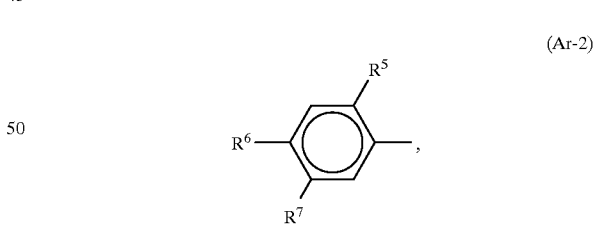

(Ar-2)

wherein: $R^5$ is hydrogen or halogen, $R^6$ is hydrogen, halogen, nitro, cyano or $YR^8$, $R^7$ is hydrogen, lower alkyl, haloalkyl,

wherein X is O, $S(O)_m$, $NR^8$ or $CR^8R^9$; Y is O, $S(O)_m$, $NR^8$; m is 0–2; and $R^8$ and $R^9$ are as defined for Formula Ar-1. In a still more preferred embodiment, $R^5$ is halogen, $R^6$ is halogen, $R^7$ is lower alkyl, haloalkyl, or

where W is hydrogen, hydroxy, halogen, or —$OC_{1-5}$ alkyl.

The acetophenones of Formula IIIa are known in the art. For example, 2,4-dihalo-5-methyl-acetophenones of Formula Ia may be prepared from commercially available 2,4-dihalogenated toluene. Briefly, the substituted toluene may be acylated using an acylating agent such as an acyl halide, an anhydride or a ketene in the presence of a Lewis acid or Bronstead acid at temperatures ranging from about −50° C. to about 200° C. and preferably from about 0° C. to about 100° C. The amount of acylating agent preferably ranges from one molar equivalent to an excess, and preferably an excess of about 2 molar equivalents relative to the amount of substituted toluene. The acylation reaction may be carried out neat or in any inert solvent. Prefered solvents include nitrobenzene, carbon disulfide, organic acids or halogenated hydrocarbons. The reaction may be carried out under pressure, with pressures ranging from about $1\times10^5$ Pa (about 1 psig) to about $1.7\times10^5$ Pa (about 10 psig). Reaction time varies depending on reagent concentrations, temperature, etc. The preparation of phenyl-diketones of Formula IIIb from such acetophenones may be carried out substantially as described below for preparing compounds of Formula Ib and Formula IIb.

In a more preferred process, phenyl-diketones of Formula Ib are prepared from acetophenones of Formula Ia according to the reaction

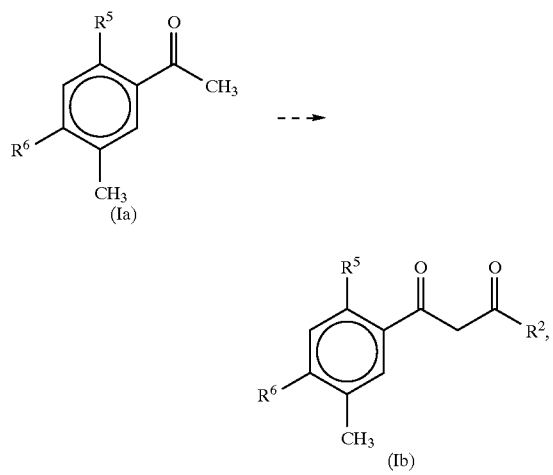

wherein $R^2$ is $C_{1-3}$ haloalkyl and $R^5$ and $R^6$ are halogen, by acylating a compound of Formula Ia with an acylating agent. A suitable acylating agent is a haloacylhalide structurally represented as the compound of Formula A1,

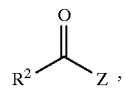

(A1)

wherein Z is halogen and $R^2$ is $C_{1-3}$ haloalkyl. The haloacylhalide preferably has a fully halogenated α-carbon, such that after acylation and after subsequent formation of the pyrazole ring, the $R^2$ carbon nearest the pyrazole ring is fully halogenated. The complete halogenation of this carbon favorably affects the herbicidal activity of compounds of Formula I. Moreover, the full halogenation of this $R^2$ carbon also facilitates synthesis of the desired regioisomer, as noted below (Process B). The haloacylhalide is preferably a haloacetylhalide, more preferably a trihaloacetylhalide, even more preferably a trihaloacetylchloride and most preferably trifluoroacetylchloride. (Example 1, Process A). Another suitable acylating agent is an alkyl haloacetate, with alkyl trihaloacetates being preferred and methyl or ethyl trifluoroacetate being most preferred. Haloacylhalides and alkyl haloacetates are equally preferred as acylating agents in terms of reactivity or yield, but the use of haloacylhalides presently offer a cost advantage over alkyl trihaloacetates.

Compounds of Formula Ib may be prepared in any anhydrous solvent or mixture of solvents, including ether, alcohols, dimethylsulfoxide, toluene, benzene, etc, with alcohol being a preferred solvent. The reaction is preferably carried out in the presence of a strong base such as an alkali alkoxide, alkali amide or alkali hydride, with alkali alkoxides such as sodium methoxide being preferred. The use of alcohol/alkali alkoxide solvent mixtures generally results in better yields, and higher substrate payloads.

Preferably, a slight excess of acylating agent (1.2 to 1.5 molar equivalents relative to the amount of acetophenone to be reacted) is premixed with an excess of a 75% methanol/25% sodium methoxide solution (about 1.5 molar equivalents of sodium methoxide relative to the amount of acetophenone) to form a reagent mixture. To accommodate the exothermic mixing, the initial temperature of methanol/sodium methoxide solution, prior to mixing, ranges from about −20° C. to about 60° C., more preferably from about −10° C. to about 20° C. and is most preferably about −5° C. The temperature is controlled during the mixing and before addition of the acetophenone to be less than about 60° C. and more preferably less than about 40° C. The substituted acetophenone is then added to the reagent mixture, followed by the further addition of methanol/sodium methoxide solvent (another 1.5 molar equivalents relative to the amount of acetophenone). The reaction proceeds at atmospheric pressure and at temperatures ranging from about 25° C. to about 75° C., more preferably from about 50° C. to about 70° C. and most preferably at about 60° C. The reaction time varies from about a few minutes to several days, depending primarily on the concentration of the reagents and the reaction temperature. Yields of greater than about 90% are typically achieved using reaction times of about 45 minutes at 60 ° C.

While the haloacylhalide is preferably premixed with the alkoxide/alcohol solution prior to adding the acetophenone substrate, the order of combining the acylating agent, substrate, and solvent or solvent mixture is not narrowly critical. For example, the reaction could also be effected by premixing the acetophenone substrate with a basic solvent and then adding the acylating agent, or as a further alternative, by adding the acylating agent and acetophenone at the same time. One consideration in determining a preference of order relates to controlling exotherms which result upon combination of reagent, substrate and solvents.

Upon completion of the reaction, the compound of Formula Ib may, if desired, be isolated and/or purified. The resulting compound is precipitated out of solution by cooling the reaction mixture to about 50° C., neutralizing with a mineral acid solution such as a 10% Hcl solution, and further cooling to about 10° C. The precipitated product can then be isolated by filtration, and, if desired, purified by methods known in the art, such as crystallization.

Where the phenyl-diketone of Formula Ib will be subsequently used in Process B, however, several alternative work-up schemes may be suitably employed to replace the solvent system used in Process A (e.g. alcohol/alkali alkoxide) with the system to be subsequently used in Process B (e.g. aromatic solvents). For example, the compound of Formula Ib may be precipitated and isolated as described above, and the isolated phenyl-diketone precipitate can be reslurried into the solvent to be used for Process B, without further drying or purification. More preferably, the reaction mixture is worked up without isolating the phenyl-diketone product. Where an alcohol/alkali alkoxide solvent is to be replaced with an aromatic solvent, the work-up preferably includes neutralizing the reaction mixture with a mineral acid solution as a 10% Hcl solution and stripping the alcohol at temperatures ranging from about 45° C to about 50° C. under a slight vacuum. At least about 50% of the alcohol should be removed, preferably at least about 80% is removed and most preferably at least about 90% is removed. The aromatic solvent is then added and the aqueous layer is removed. A variation of this method includes first stripping the alcohol under reduced pressure, cooling the reaction mixture to about ambient temperature, adding the aromatic solvent, washing with an aqueous mineral acid solution, further washing with deionized water and removing the resulting aqueous phase. In either of the latter two aforementioned work-up schemes, the organic phase contains the desired phenyl-diketone product and is used in Process B, as described below.

In a most preferred embodiment, a phenyl-diketone of Formula IIb is prepared from an acetophenone of Formula IIa according to the reaction:

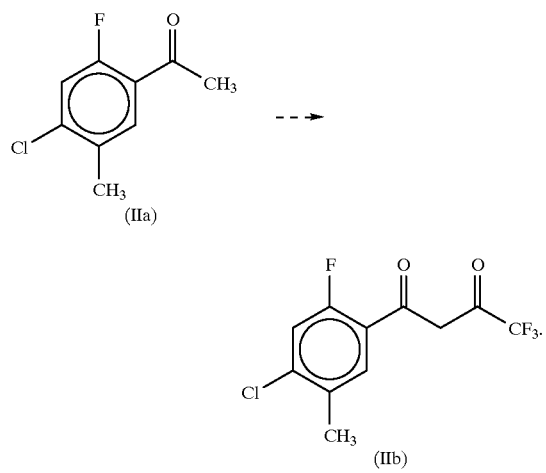

This reaction is carried out substantially as described above for preparing compounds of Formula Ib, using either trifluoroacetylchloride, methyl trifluoroacetate or ethyl trifluoroacetate as the acylating agent. Trifluoroacetylchloride is presently less expensive than methyl or ethyl trifluoroacetate, and is therefore preferred with respect to cost, but the aforementioned acylating agents are otherwise equally preferred. The preparation of compounds of Formula IIb is further exemplified in Example 1 (Process A).

Process B

Process B relates to the cyclization of phenyl-diketones and subsequent alkylation to form alkylated 3(5)-aryl-5(3)-haloalkyl pyrazoles. In the general case, an aryl-pyrazole of Formula IIIb may be converted to an alkylated 3-aryl-pyrazole of Formula IIId according to the reaction

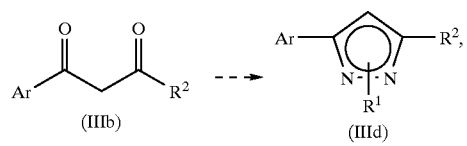

wherein: Ar is phenyl or substituted phenyl as defined for Process A; $R^1$ is alkyl or alkyl substituted with halogen, amino, nitro, cyano, hydroxy, carboxy, alkoxy, thio, mercaptoalkyl or alkylthio; and $R^2$ is alkyl, hydroxy, alkoxy, acyl, carboxylic acid and aldehyde, amide and ester derivatives thereof, halogen, haloalkyl, amino, nitro, cyano, mercaptoalkyl, alkylthio, alkylsulfinyl, alkylsulfonyl, alkylphosphinyl or alkylphosphonyl. $R^1$ is preferably $C_{1-5}$ alkyl and $R^2$ is preferably a $C_{1-3}$ haloalkyl. This reaction is effected by condensing a compound of Formula IIIb with hydrazine and preferably with an excess of hydrazine, removing any excess hydrazine, and alkylating, as described in detail below for preparing compounds of Formula Id and IId. If desired, an intermediate compound of the Formula IIIc

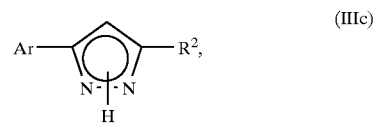

wherein Ar and $R^2$ are as defined above for compounds of Formulae IIIb and IIId, may be formed by condensing the phenyl-diketone of Formula IIIb under acidic conditions or adding an acid to the reaction mixture after the condensation. The alkylation reaction may be carried out regioselectively, under acidic conditions, without deprotonating the N-hydrogen of Formula IIIc, to form the 3-aryl-isomer of Formula IIIe,

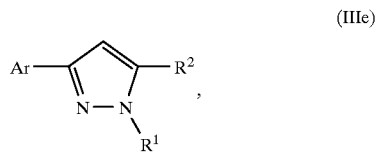

wherein Ar and $R^1$ are as defined above for compounds of Formulae IIIb and IIId and wherein $R^2$ is alkyl, hydroxy, alkoxy, acyl, carboxylic acid and aldehyde, amide and ester derivatives thereof, halogen, haloalkyl, amino, nitro, cyano, mercaptoalkyl, alkylthio, alkylsulfinyl, alkylsulfonyl, alkylphosphinyl or alkylphosphonyl.

Process B particularly relates to the regioselective preparation of 3-aryl-5-haloalkyl pyrazoles of Formula Id according to the overall reaction:

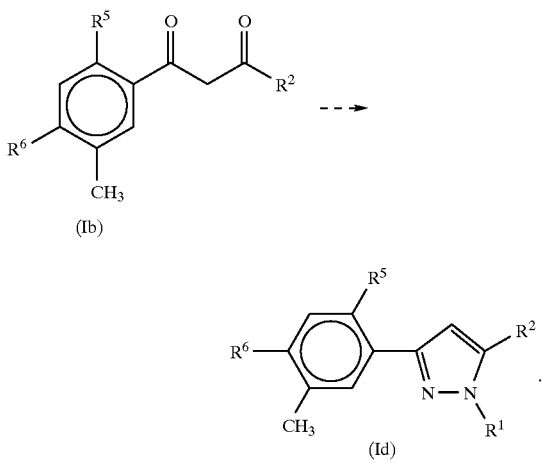

(Ib)

(Id)

wherein $R^1$ is $C_{1-5}$ alkyl, $R^2$ is $C_{1-3}$ haloalkyl and $R^5$ and $R^6$ are halogen. A phenyl-diketone of Formula Ib is condensed with hydrazine in a reaction mixture to form one or more intermediates, discussed in detail below and collectively referred to as alkyl-pyrazole-precursor intermediates. An alkylating agent is then added to the reaction mixture and reacts with the alkyl-pyrazole-precursor intermediate(s) to form, in the general case, a mixture of two isomers, collectively represented by Formula Ic,

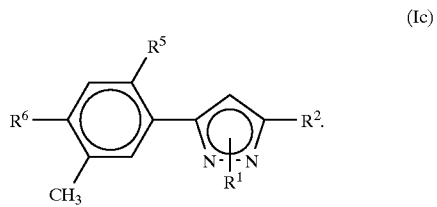

(Ic)

Advantageously, when the alkylation reaction is carried out under acidic conditions and/or with an electron withdrawing moiety as the $R^2$ group, the predominant product formed is the 1-alkyl-3-aryl-5-haloalkyl-pyrazole (Formula Id) rather than the 1-alkyl-5-aryl-3-haloalkyl-pyrazole, referred to hereinafter as the 3-aryl isomer and the 5-aryl isomer, respectively.

The hydrazine is preferably unsubstituted hydrazine. While alkyl-substituted hydrazines such as methylhydrazine could be used in the present invention to form an alkylated pyrazole in a single step, the regioisomer resulting therefrom is predominantly the 5-aryl isomer rather than the desired 3-aryl isomer. Hydrazine may be reacted with the phenyl-diketone of Formula Ib in any suitable solvent or mixture of solvents, including both organic and aqueous solvents. Based on availability and cost, hydrazine is preferably used in the reaction as an aqueous solution. To facilitate subsequent work-up steps, the phenyl-diketone is preferably in an organic solution. Aromatic solvents having a relatively high boiling point such as toluene, xylene, cymene, cumene and ethyl benzene are preferred, with toluene being a most preferred solvent for the phenyl-diketone.

The reaction is most preferably effected by adding an aqueous hydrazine solution to a toluene solution containing the phenyl-diketone to form a two-phase reaction mixture in which the phenyl-diketone is in an organic phase and hydrazine in an aqueous phase. The toluene solution is preferably at about ambient temperature when the hydrazine solution is added. Sufficient hydrazine solution is added to provide a stoichiometric excess amount of hydrazine in the reaction mixture relative to the phenyl-diketone. For purposes herein, the stoichiometric excess amount is the residual amount of hydrazine which would remain after all of the phenyl-diketone has completely reacted with hydrazine. Equivalently, the stoichiometric excess amount of hydrazine in the reaction mixture or reaction zone at any given time is the difference between the molar amount of hydrazine present at that time and the molar amount of phenyl-diketone present at that time. The amount of excess hydrazine present in the reaction mixture is preferably at least about 1 mole percent of a reference amount, the reference amount being the sum of the molar amount of unreacted phenyl-diketone and the molar amount of alkyl-pyrazole-precursor intermediate formed. The amount of excess hydrazine is more preferably at least about 15 mole percent of the reference amount, and is most preferably about 20 mole percent of the reference amount. While upper limits are not narrowly critical, the amount of excess hydrazine preferably ranges from about 5 to about 50 mole percent and more preferably from about 10 to about 25 mole percent. The use of excess hydrazine maximizes the conversion of the phenyl-diketone to alkyl-pyrazole-precursor intermediate, thereby resulting in improved yields. After adding the hydrazine solution, the reaction mixture is stirred to facilitate the inter-phase reaction between hydrazine and the phenyl-diketone. The reaction mixture may also contain some unreacted acetophenone carried over from the previous step (Process A). The reaction is preferably effected at atmospheric pressure and at temperatures ranging from about 0° C. to about 60° C., more preferably at temperatures ranging from about 30° C. to about 50° C. and most preferably at a temperature of about 40° C. Reaction times vary from about a few minutes to several days depending on the concentration of the reagents and the reaction temperature. At 40° C., the reaction is completed, as determined by gas chromatography, within about 30 minutes.

Without being bound by theory, one or more intermediate compounds are believed to result from condensation of the phenyl-diketone (Formula Ib) with hydrazine. For example, 3-aryl-5-hydroxy-pyrazolines of Formula B1 or 3(5)-aryl-pyrazoles of Formula B2

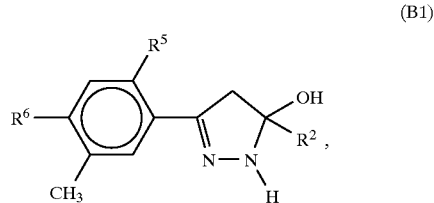

(B1)

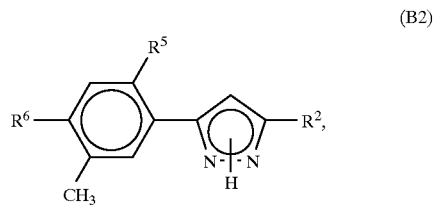

(B2)

are likely to form, depending on the reaction conditions employed. Compounds of Formula B1 are thought to be the predominant intermediate when the condensation reaction is carried out under neutral conditions, whereas compounds of Formula B2 are thought to predominate under acidic conditions. Hence, while it is not necessary to isolate and/or characterize the alkyl-pyrazole-precursor intermediate compounds for purposes of the present invention, aryl-pyrazole intermediates of Formula B2 may be obtained by allowing the aforementioned condensation reaction to proceed under acidic conditions (e.g. using an acetic acid solvent as in Example 2) or, alternatively, by adding acid to the reaction mixture after the condensation reaction is completed. Regardless of the exact structure of the intermediate(s) formed as the condensation reaction proceeds, the phenyl-diketone reagent and the resulting intermediate(s) remain preferentially in the organic phase of the reaction mixture, while hydrazine remains in the aqueous phase thereof. However, some resulting intermediate may precipitate out of solution.

Upon completion of the condensation reaction, the excess hydrazine and the resulting alkyl-pyrazole-precursor intermediates are preferably separated from each other before alkylating the intermediates to form alkylated pyrazole compounds of Formulas Ic or Id. Such separation minimizes the explosive danger which would exist if the resulting intermediate(s) were alkylated in the presence of hydrazine. The separation may be effected by any means known in the art, but is preferably effected by phase separation (in two-phase reaction mixtures) or by liquid-liquid solvent extraction methods (in single-phase reaction mixtures). Excess hydrazine is preferably removed from the reaction mixture without isolating the resulting intermediate(s). Where the reaction mixture is the preferred two-phase system described above, the excess hydrazine is removed from the reaction mixture by first heating the reaction mixture to redissolve into the organic phase any amount of precipitate which may have formed during the reaction. Such heating also facilitates separation of the aqueous phase from the organic phase into separate aqueous and organic layers. If desired, other solvents may be added to the two-phase system to either increase the partition coefficients or sharpen phase separation. The aqueous phase layer, which includes hydrazine, is then removed from the reaction mixture. The remaining organic phase may be further washed with an aqueous solution, such as a brine (NaCl) solution. This wash solution is also separated and removed from the organic solution. In an alternative two-phase system, the resulting intermediate (s) and the excess hydrazine may be separated from each other by removing organic phase containing the resulting intermediate(s) from the reaction mixture. Alternatively, the reaction can be carried out in a single-phase organic system, in which anhydrous hydrazine is reacted with a phenyl-diketone of Formula Ib and the excess hydrazine is removed by extraction with water. If the reaction is instead carried out in a single phase aqueous solution, the resulting intermediate (s) may be separated by extraction with an organic solvent. The phase separation and liquid-liquid extraction work-up steps described herein are less cumbersome than isolation or purification techniques (e.g. precipitation and/or crystallization) and safer than distillation methods.

After condensing the phenyl diketone (Formula Ib) with hydrazine and removing any excess hydrazine, an alkylating agent is added to the reaction mixture to alkylate the alkyl-pyrazole-precursor intermediate(s). The resulting alkylated pyrazole is represented generally by Formula Ic. Suitable alkylating agents include alkyl halides, alkyl sulfonates and mono- or di-alkylsulfates, with dialkylsulfates being preferred. When $R^1$ is a methyl group, dimethylsulfate, methyliodide, and methylbromide are preferred alkylating agents. Dimethylsulfate should be used in at least an equimolar amount relative to the phenyl-diketone of Formula Ib, as the second methyl group is not reactive enough to alkylate the intermediate(s). The alkylating agents are preferably added to the reaction mixture in molar excess relative to the amount phenyl-diketone being reacted, the molar excess ranging from about 1.01 to about 1.3 molar equivalents, more preferably from about 1.05 to about 1.25 molar equivalents and most preferably from about 1.1 to about 1.2 molar equivalents. The alkylating agents should generally be added slowly to the reaction mixture to help avoid large exothermic excursions.

While the alkylation could be carried out under neutral, basic or acidic conditions, acidic conditions are preferred to maximize the regioselective preparation of the desired 3-aryl isomer of Formula Id. (Example 3). Significantly, the percentage of the 3-aryl isomer obtained under acidic conditions is consistently greater than about 90% of the total amount of aryl-pyrazole product, and frequently greater than about 95%, whereas under non-acidic conditions, the percentage of 3-aryl isomer obtained ranged from about 55% to about 80%. Without being bound by theory, this selectivity is believed to arise from the fact that intermediates such as the compound of Formula B2 exist predominantly (greater than about 90%) in the 5-aryl tautomeric form (Formula B3) and only marginally (less than about 10%) in the 3-aryl form (Formula B4):

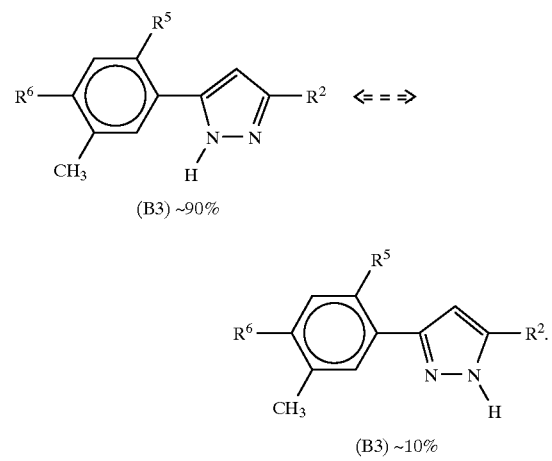

(B3) ~90%

(B3) ~10%

Under basic conditions, the nitrogen is believed to be deprotonated, leaving a very reactive electron pair for alkylation. Since the deprotonated nitrogen is predominantly the nitrogen closest to the aryl group, the 5-aryl isomer dominates under basic conditions. In contrast, when the alkylation is carried out under acidic conditions, no deprotonation occurs and the other nitrogen (ie, the nitrogen lacking hydrogen) is relatively more reactive. Hence, the alkylation is selective to form the 3-aryl isomer under acidic conditions. Acidic conditions are also preferred over basic conditions with regard to the stability of: the reaction for particular $R^2$ constituents, such as $CF_2Cl$. (Example 4).

The selective preparation of the 3-aryl isomer is also favorably influenced by the electron-withdrawing capability of the $R^2$ group. Electron withdrawing $R^2$ moieties which enhance selective alkylation include substituted alkyl, acyl, carboxylic acid and aldehyde, amide and ester derivatives thereof, halogen, haloalkyl (Example 3), nitro, cyano, mercaptoalkyl, alkylthio, alkylsulfinyl, alkylsulfonyl, alkylphosphinyl or alkylphosphonyl. The $R^2$ group is preferably a haloalkyl group and most preferably a haloalkyl group which is fully halogenated at the carbon closest to the pyrazole ring. The aryl group has relatively little effect on regioselectivity.

Preferred solvents for the alkylation reaction include toluene, xylene, cymene, acetone, dimethylsulfoxide, dimethylformamide, dioxane, etc, with toluene being most preferred. The alkylation is most preferably effected by reacting the intermediate(s) with a dialkylsulfate in anhydrous toluene under reflux conditions. The toluene solvent may be neutral prior to the reaction, but acidic conditions are immediately generated as the alkylation reaction proceeds under reflux. For example, where dimethylsulfate is used as the alkylating agent, methyl-sulfonic acid is generated as soon as methylation of the intermediate(s) begins. Alternatively, to ensure acidic conditions before the start of the reaction, a small amount of acid such as p-toluene sulfonic acid can be added. The reaction is preferably carried out under atmospheric pressure and at a temperature ranging from about 60° C. to about 120° C., and most preferably at about 105° C. As the alkylation reaction proceeds, water is removed from the reaction mixture as a toluene/water azeotrope. The azeotrope is preferably condensed and the condensate separated, with the toluene being returned to the reaction mixture. The progress of the reaction may be monitored using gas chromatography, and, if necessary, additional alkylating agent may be added to effect complete conversion to the alkylated pyrazole. Reaction times may range from about a few minutes to several days depending on the concentration of the reagents and the reaction temperature. Overall yields ranging from about 70% to about 85% are typically achieved using reaction times of about 16 hours at a temperature of about 105° C.

After the reaction is completed, the product may be isolated and purified by methods known in the art, including precipitation and filtration, concentration, extraction, crystallization or chromatographic methods. The reaction product mixture is preferably worked up by cooling to about 50° C. and then washing in succession with caustic solutions (5% NaOH, then 10% NaOH) to destroy any excess dimethylsulfate and to neutralize the organic phase. The product mixture is then further washed with a brine solution (10%). The toluene solvent is then replaced with methanol by stripping toluene in vacuo and adding methanol. The 3-aryl regioisomer is isolated by adding water (16:1 methanol:H$_2$O), cooling to a temperature of about 5° C. to about 10° C. and centrifuging to crystallize the desired 3-aryl isomer while leaving the undesired 5-aryl isomer in solution.

In a most preferred embodiment, the alkylated 3-aryl-pyrazole of Formula IId is prepared from the phenyl diketone of Formula IIb according to the reaction:

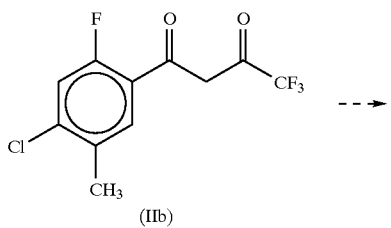
(IIb)

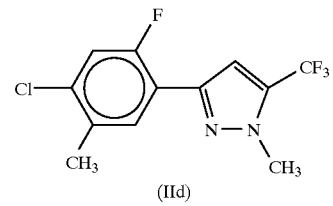
(IId)

This reaction is carried out substantially as described above for preparing compounds of Formula Id, and is further exemplified in Example 1 (Process B).

Process C

Process C relates to the oxidation of alkyl-substituted benzene compounds to form the corresponding benzoic acids. While the substrate for this reaction is preferably a 2,4-dihalo-5-pyrazole toluene, the oxidation method of the present invention is more generally applicable to other alkyl-substituted benzene substrates, including for example, unsubstituted toluene, substituted toluene, substituted toluene where at least one substituent is a substituted or unsubstituted heterocyclic ring having up to 6 ring members, and substituted toluene where at least one substituent is pyrazole or substituted pyrazole. In particular, the oxidization method of the present invention may be used to prepare a substituted-benzoic acid pyrazole of Formula IIIg from a substituted-toluene of Formula IIIf according to the reaction

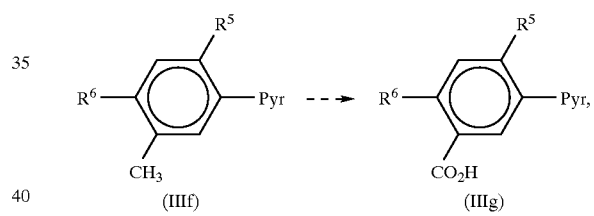

wherein in the above formulae, $R^5$ and $R^6$ are halogen and Pyr is a substituted or unsubstituted pyrazole.

The term "substituted pyrazole" as used herein means a substituted pyrazole of Formula Pyr-1,

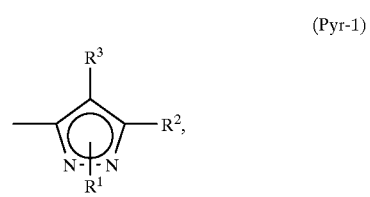
(Pyr-1)

wherein in the above formula, $R^1$ is hydrogen, alkyl or alkyl substituted with halogen, amino, nitro, cyano, hydroxy, carboxy, alkoxy, thio, mercaptoalkyl or alkylthio; $R^2$ is alkyl, hydroxy, alkoxy, acyl, carboxylic acid and aldehyde, amide and ester derivatives thereof, halogen, haloalkyl, amino, nitro, cyano, mercaptoalkyl, alkylthio, alkylsulfinyl, alkylsulfonyl, alkylphosphinyl or alkylphosphonyl; and $R^3$ is hydrogen or halogen. The substituted pyrazole is more preferably the 1-alkyl-5-aryl isomer of Formula Pyr-2,

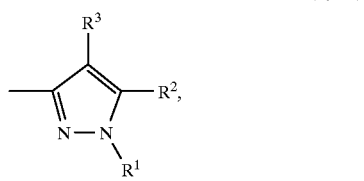

(Pyr-2)

wherein in the above formula, $R^1$ is hydrogen or $C_{1-5}$ alkyl; $R^2$ is hydrogen or $C_{1-3}$ haloalkyl; and $R^3$ is hydrogen or halogen.

Substituted-toluenes of Formula IIIf are oxidized to form benzoic acids of Formula IIIg substantially as detailed below for preparing compounds of Formula Ie and IIe.

In a preferred embodiment of Process C, benzoic acid compounds of Formula Ie are prepared by oxidizing 2,4-dihalo-5-pyrazole-toluene compounds of Formula Id according to the reaction:

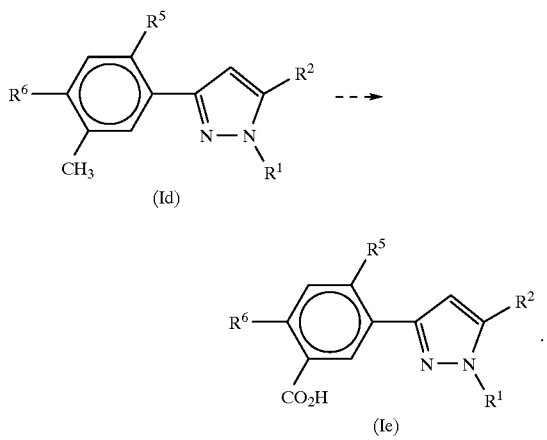

wherein $R^1$ is $C_{1-5}$ alkyl, $R^2$ is $C_{1-3}$ haloalkyl, and $R^5$ and $R^6$ are halogen. The reaction is preferably carried out as a direct oxidation by reacting the compound of Formula Id with molecular oxygen in the presence of metal salt catalyst or mixtures thereof, catalyst promoter and free radical initiator. As detailed below, the use of benzoyl peroxide as the initiator of this reaction provides for a more robust and reliable reaction relative to prior art initiators.

A variety of metal salt catalysts such as cobalt salts, manganese salts, nickel salts, cesium salts and zirconium salts may be used individually or in combination. Examples of such salts include cobalt (II) acetate, cobalt formate, cobalt hexylate, cobalt chloride, cobalt carbonate, cobalt acetylacetonate, manganese (II) acetate, manganese chloride, cesium (III) acetate, zirconium (IV) acetylacetonate, zirconium chloride, nickel chloride, etc. Cobalt acetate, Co(OAc)$_2$, manganese acetate, Mn(OAc)$_2$ or co-catalysts thereof are preferred catalysts. The total amount of a single catalyst or of a combination of catalysts in a mixture can range from about less than 1% to about 100% molar equivalents relative to the compound of Formula Id.

A catalyst promoter is used in conjunction with the metal salt catalyst. Preferred catalyst promoters include alkyl halides, halide salts, lithium salts, carboxylate salts, with halide salts such as alkali halides and ammonium halides being more preferred. Bromide compounds such as sodium bromide, hydrogen bromide and ammonium bromide are most preferred as catalyst promoters. The amount of halide salt promoter preferably ranges from about 0.1 mole % to about 10 mole % relative to the compound of Formula Id. A ketone such as acetone may be used as a catalyst promoter or as a co-promoter with the halide salt promoter. Without being bound by theory, it appears that acetone hastens the typically slow induction period of the reaction, thereby shortening the total reaction time by as much as 20% to 30%.

While any known initiator, such as hydrogen peroxide, is suitable to initiate the oxidation reaction, benzoyl peroxide is a preferred initiator. Advantageously, the use of benzoyl peroxide makes the reaction more robust, dependable and reliable relative to the use of hydrogen peroxide, which is substantially less reliable and often erratic with regard to initiating the oxidation. Without being bound by theory, it is believed that the benzoyl peroxide makes the reaction less sensitive to impurities which commonly stall the reaction. The amount of benzoyl peroxide used preferably ranges from about 0.1 mole % to about 10 mole % relative to the substituted toluene compound of Formula Id, more preferably from about 0.1 mole % to about 5 mole % and most preferably from about 0.3 mole % to about 0.7 mole %.

The reaction is preferably carried out: in any suitable solvent which does not interfere with the course of the reaction; however, the reaction can also be carried out neat. Preferred solvents include aliphatic carboxylic acids and anhydrides such as acetic acid and acetic anhydride. Acetic acid is a most preferred solvent.

The substrate compound of Formula Id is preferably combined with the catalyst, promoter and initiator in a suitable reactor and mixed. A most preferred reaction mixture includes the substrate and the following combination of co-catalysts, catalyst promoters and initiator in acetic acid: from about 0.9 to about 1.1 mole percent Co(OAc)$_2$, from about 0.09 to about 0.11 mole percent Mn(OAc)$_2$, from about 2.7 to about 3.3 mole percent sodium bromide, from about 4.5 to about 5.5 mole percent acetone and from about 0.6 to about 0.8 mole percent benzoyl peroxide. Molecular oxygen is supplied to the reaction mixture in stoichiometric excess as pure O$_2$, as air, or as a mixture of oxygen or air in other gasses. Without being bound by theory, the rate of reaction appears to be mass transfer limited. As such, the mixture should be well mixed or agitated during the reaction to maximize oxygen dispersion. The reaction may proceed at atmospheric pressure, or, if desired, in a pressurized atmosphere. When oxygen is used in a pressurized system, the oxygen pressure preferably ranges from about 1×10$^5$ Pa to about 70×10$^5$ Pa (about 1 atm to about 1000 psig) and more preferably from about 1×10$^5$ Pa to about 18×10$^5$ Pa (about 1 atmosphere to about 250 psig). The oxygen pressure is most preferably about 1.7×10$^5$ Pa (about 10 psig). When air is used, the above-recited pressure values represent the partial pressure of oxygen in the air. While higher pressures favorably influence the reaction rate, the capital costs required to effect such pressurization may negate any overall benefit to conducting the reaction at higher pressures. The reaction preferably proceeds at temperatures ranging from about 80° C. to the boiling point of the solvent. When acetic acid is used as the solvent, the reaction temperature preferably ranges from about 80° C. to about 120° C., with a temperature of about 110° C. being preferred. Reaction times may range from about a few minutes to several days depending on the concentration of the reagents and the reaction temperature. Yields of about 90% are typically achieved in about 5 to 50 hours at a temperature of about 110° C.

After the reaction is completed, the product may be isolated and purified using conventional methods. However, where the resulting benzoic acid of Formula Ie will be used in subsequent steps of the overall process, the product is preferably not isolated from solution prior to the next step (Process D). When use in the subsequent step is anticipated, the reaction mixture is kept at a temperature of greater than about 70° C. to minimize the potential for product precipitation.

In a most preferred embodiment, the benzoic acid of Formula IIe is prepared from the aryl-pyrazole of Formula IId according to the reaction:

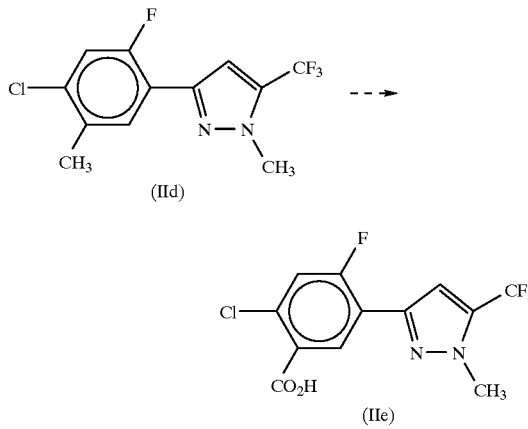

This reaction is carried out substantially as described above for preparing compounds of Formula Ie, and is further exemplified in Example 1 (Process C). In this reaction, the methyl group on the aryl member of Formula IId is oxidized preferentially relative to the methyl on the pyrazole member. Typically, only about 1–2% of the product has the methyl group on the pyrazole oxidized. To prevent further oxidation of the pyrazole-methyl, however, the reaction should be discontinued once all of the aryl-methyl has been reacted. For example, once all of the substrate compound has reacted, as determined by HPLC sampling, the reaction may be terminated by cutting off oxygen supply and, if the system is pressurized, venting the reactor.

Process D

Process D relates to the halogenation of heterocyclic compounds. While the substrate for this reaction is preferably a 1-alkyl-3-aryl-5-haloalkylpyrazole, the bromination method of the present invention is more generally applicable to other heterocyclic substrates, including heterocyclic compounds having up to 6 ring-members, unsubstituted pyrazoles, or substituted pyrazoles. In particular, the bromination method of the present invention may be used to prepare a phenyl-substituted pyrazole of Formula IIIh from a compound of Formula IIId according to the reaction

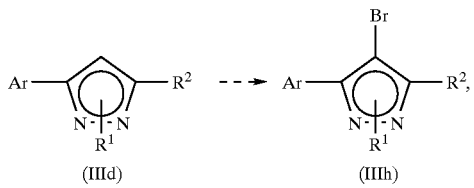

wherein: Ar is phenyl or substituted phenyl as defined in Process A; $R^1$ is hydrogen, alkyl or alkyl substituted with halogen, amino, nitro, cyano, hydroxy, carboxy, alkoxy, thio, mercaptoalkyl or alkylthio; and $R^2$ is alkyl, hydroxy, alkoxy, acyl, carboxylic acid and aldehyde, amide and ester derivatives thereof, halogen, haloalkyl, amino, nitro, cyano, mercaptoalkyl, alkylthio, alkylsulfinyl, alkylsulfonyl, alkylphosphinyl or alkylphosphonyl. More preferably, $R^1$ is hydrogen or $C_{1-5}$ alkyl and $R^2$ is $C_{1-3}$ haloalkyl. The bromination of such substrates is carried out substantially as described below for preparing compounds of Formula If and IIf.

Process D relates, more preferably, to the halogenation 1-alkyl-3-aryl-5-haloalkyl pyrazoles to form 4-halo pyrazoles. The halogenated pyrazoles of Formula If are prepared by halogenating a compound of Formula Ie according to the reaction

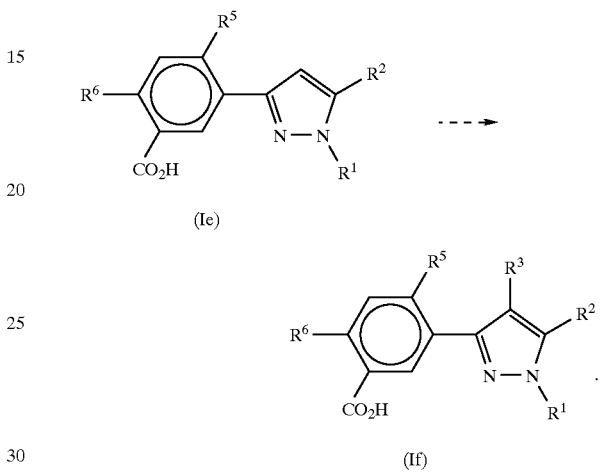

wherein $R^1$ is $C_{1-5}$ alkyl, $R^2$ is $C_{1-3}$ haloalkyl, and $R^3$, $R^5$ and $R^6$ are halogen. Suitable halogenating agents known in the art include chlorine, N-chlorosuccinimide, sulfuryl chloride, bromine, N-bromosuccinimide, etc. The amount of halogenating reagent can range from less than one molar equivalent to an excess, relative to the 3-aryl pyrazole compounds of Formula Ie. Any inert solvent may be used, including organic acids, inorganic acids, hydrocarbons, halogenated hydrocarbons, aromatic hydrocarbons, ethers, sulfides, sulfoxides and sulfones. Reaction temperatures may range from about 10° C. to about 100° C. and the reaction period will vary depending on reagent concentrations, temperature, etc.

$R^3$ is preferably a bromo group, and Process D relates, in a preferred embodiment, to the bromination of heterocyclic compounds such as a 1-alkyl-3-aryl-5-haloalkyl pyrazole. A compound of Formula Ie may be brominated to prepare a brominated pyrazole of Formula If (with $R^3$ as bromo), by reacting the compound of Formula Ie with a bromonium ion. The bromonium ion is preferably generated by oxidizing a bromide salt. Both organic and inorganic bromide salts are suitable, with inorganic bromide salts such as alkali bromides (e.g. sodium bromide) being preferred. Preferred oxidizing agents include, independently, aqueous sodium hypochlorite and chlorine gas. The bromonium ion may, alternatively, be present as bromonium chloride, BrCl, formed for example by mixing $Br_2(g)$ and $Cl_2(g)$. Advantageously, bromonium ion generated from a bromide salt under oxidizing conditions is generally more reactive and more selective than liquid bromine. Reaction times using this system are shorter than those using liquid bromine by an order of magnitude. Moreover, the bromination reagents used herein are generally less expensive than liquid bromine, and the present method minimizes the quantity of bromide waste which is generated.

The reaction may be carried out in any suitable solvent, but is preferably conducted using aliphatic acid solutions such as acetic acid. The use of an acetic acid solution helps minimize undesired side reactions, such as halogenation of the benzoic acid to an acid halide.

Preferably, excess sodium bromide is added to an acetic acid solution containing a compound of Formula Ie. The total amount of sodium bromide in the reaction mixture preferably ranges from about 1.0 to about 1.6 molar equivalents relative to the amount of benzoic acid substrate of Formula Ie, more preferably from about 1.15 to about 1.5 molar equivalents with about 1.4 equivalents being most preferred. Note that when the reagent compound of Formula Ie is supplied directly from the previous oxidation step, the existing mixture may already contain a relatively small amount of NaBr which was used as a promoter during oxidation. In such a case, the amount of NaBr already existing in solution should be accounted for in determining the amount of NaBr to add. The sodium bromide is preferably added as an aqueous solution formed by dissolving the NaBr in distilled or deionized water (about 17 to about 25 molar equivalents $H_2O$, with about 21 molar equivalents being preferred). The reaction mixture should be well mixed while adding NaBr and during the subsequent reaction to achieve good bromination yield and minimize side reactions. The sodium bromide is preferably added slowly to minimize the formation of large lump precipitates and to minimize significant temperature departures below about 70° C. The oxidation agent is added and the reaction mixture is heated to the desire reaction temperature, which preferably ranges from about ambient temperature to about 100° C., more preferably from about 70° C. to about 90° C. and most preferably from about 75° C. to about 85° C.

When chlorine gas is used as the oxidizing agent, excess chlorine is slowly added, while mixing, to the reaction mixture. The amount of excess chlorine preferably ranges from about 1.0 to about 1.5 molar equivalents relative to the amount of heterocyclic substrate of Formula Ie. When the oxidized aryl-pyrazole product resulting from Process C is subsequently brominated in the instant process without being isolated, the amount of excess chlorine preferably ranges from about 1.0 to about 1.3 molar equivalents relative to the amount of substituted toluene substrate of Formula Id (Process C), with about 1.15 molar equivalents being most preferred. Without being bound by theory, it is believed that the chlorine reacts with aqueous sodium bromide to form bromonium ion, Hcl and NaCl, and the bromonium ion brominates the substrate. The reaction following the addition of chlorine gas is fairly exothermic. As the reaction progresses, the reaction mixture typically becomes more viscous, and may require higher temperatures and/or the addition of more water to facilitate proper mixing. If the reaction does not reach completion, as determined by HPLC or fluorine NMR, additional chlorine (about 0.1 molar equivalent) may be added.

When sodium hypochlorite is used as the oxidizing reagent, excess sodium hypochlorite is added after the sodium bromide has been added and mixed with the substrate compound. The NaOCl is preferably added as an aqueous solution while the reaction mixture is stirred and maintained at about 70° C. The amount of excess NaOCl preferably ranges from about 1.0 to about 3.0 molar equivalents relative to the amount of heterocyclic substrate of Formula Ie. When the oxidized aryl-pyrazole product resulting from Process C is subsequently brominated in the instant process without being isolated, the amount of excess hypochlorite preferably ranges from about 1.5 to about 3.5 molar equivalents relative to the amount of substituted toluene substrate of Formula Id (Process C), with about 2.5 molar equivalents being most preferred. The reaction then proceeds as described above with respect to using chlorine as the oxidizing agent. The sodium hypochlorite and chlorine gas are equally preferred as oxidizing agents based on performance. However, preference between these oxidizing agents may be based on other factors, such as availability. Other oxidizing agents known to those skilled in the art may also be used. Regardless of the oxidizing agent employed, the bromination reaction is preferably carried out at atmospheric pressure. Reaction times may vary from a few minutes to several days, with yields of greater than about 90% resulting in about 2–4 hours at temperatures ranging from about 75° C. to about 85° C.

When the reaction is completed, the reaction mixture is cooled to about ambient temperature or slightly greater. The excess oxidizing agent is then destroyed and the desired brominated pyrazole product is precipitated out of solution. Where the NaOCl/NaBr or Cl(g) systems are used, residual oxidizing agent may be destroyed and a precipitated product formed by adding an aqueous solution of reducing agent such as aqueous sodium sulfite solution to the reaction mixture. Additional water may be added to fully precipitate the desired product and to aid mixing. After waiting a period of time for dissolution of inorganic salts in the reaction mixture (about 15 to about 30 minutes), the precipitated product may then be filtered from solution, washed with deionized water and dried. Where the resulting halogenated pyrazole compound of Formula If will be used in the subsequent esterification step, the product should be thoroughly dried.

In a most preferred embodiment, the brominated-aryl-pyrazole of Formula IIf is prepared from the compound of Formula IIe according to the reaction:

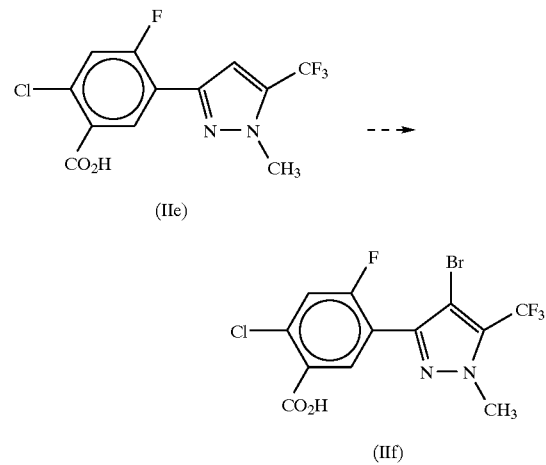

This reaction is carried out substantially as described above for preparing compounds of Formula If, and is further exemplified in Example 1 (Processes D-1 and D-2).

Process E

Process E relates to the esterification of carboxylic acids. While the substrate for this reaction is preferably a 2,4-dihalo-5-pyrazole benzoic acid, the esterification methods of the present invention are more generally applicable to other carboxylic acids, including aliphatic carboxylic acids, long-chain fatty acids, heterocyclic carboxylic acids, substituted and unsubstituted benzoic acids, and benzoic acids substituted with at least one substituent being a(n) (un)substituted heterocyclic ring having up to 6 ring members. In particular, the esterification methods presented herein may be used to prepare a benzoic acid ester of Formula IIIi from a compound of Formula IIIg according to the reaction

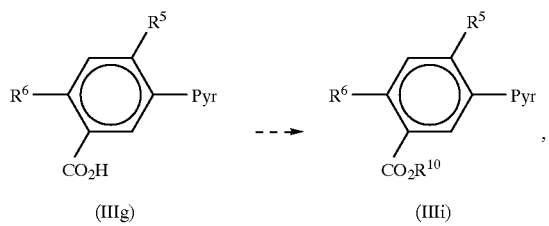

wherein Pyr is pyrazole or substituted pyrazole as defined for Process C, $R^5$ and $R^6$ are halogen, and $R^{10}$ is $C_{1-5}$ alkyl. The esterification of such substrates is carried out via either of two esterification protocols, as described in more detail below for preparing compounds of Formulas I and II.

In a more preferred process, a 2,4-dihalo-5-pyrazolebenzoic acid ester of Formula I is prepared by esterifying a compound of Formula If according to either of two protocols which effect the reaction:

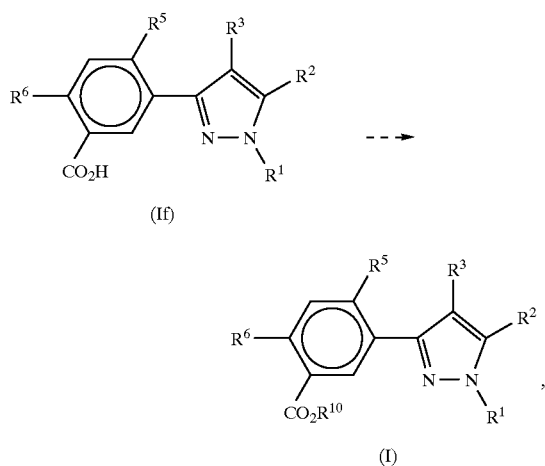

wherein $R^1$ is $C_{1-5}$ alkyl, $R^2$ is $C_{1-3}$ haloalkyl, $R^3$, $R^5$ and $R^6$ are halogen and $R^{10}$ is $C_{1-5}$ alkyl. Briefly, in a first esterification protocol, a benzoic acid of Formula If is reacted with a halogenating agent to form a corresponding acid halide. The acid halide is then stirred with an excess of esterification reagent formed by premixing an esterifying alcohol with an acyl halide. In an alternative protocol for preparing the benzoic acid ester of Formula I, the benzoic acid of Formula If is esterified with a trialkylorthoester. Each of these esterification protocols are particularly suited to esterifying with a hindered —OR group, such as isopropyl.

In the first esterification protocol, the acid halide intermediate is prepared by methods known in the art. An exemplary method includes reacting the benzoic acid substrate with a halogenating agent such as thionyl chloride, phosphorus pentachloride, oxalyl chloride, etc. Inert solvents such as toluene, which do not interfere with the halogenation reaction, may be used, and the reaction may be promoted by adding a catalytic amount of an amine base such as triethylamine, pyridine or dimethylformamide, etc. Preferably, the benzoic acid substrate is halogenated by mixing the substrate with excess halogenating agent (1.1–1.7 equivalents) in a toluene solution at ambient temperature, adding a few drops of dimethylformamide, slowly heating to about 75° C. and reacting at that temperature for about 1 to 3 hours. Other reaction temperatures and periods may be appropriate. After forming the acid halide intermediate, the toluene solvent and excess halogenating agent are removed by stripping in vacuo while maintaining the temperature at about 75° C.

The acid halide intermediate is reacted with an esterification reagent formed by mixing a small amount of an acylhalide with an alcohol of Formula $R^{10}OH$. The acyl halide is preferably a $C_{1-3}$ acyl halide, and more preferably an acetyl halide. The halide member of the acyl halide should generally be the same halide as the acid halide intermediate being esterified, and is preferably chloride. A most preferred acyl halide is acetyl chloride. The amount of acyl halide added to form the esterification agent preferably ranges from about 0.1% to about 10%, more preferably from about 2% to about 5%, and is most preferably about 4%, by weight, relative to amount of alcohol added to form the esterification agent. While not being bound by theory, acyl halides such as acetyl chloride are believed to scavenge any trace $H_2O$ which may be present in the alcohol reagent stock, thereby eliminating a potentially competing reaction when the esterifying alcohol is subsequently reacted with the acid halide intermediate being esterified. The acetyl halide appears to react preferentially with water rather than with the alcohol, particularly where the alcohol is a hindered alcohol such as isopropanol. As such, the use of a acylhalide/alcohol esterification reagent allows for the use of less expensive alcohol grades (ie, grades having from about 1% to about 2% water) while providing for improved yields and purity of the resulting ester product. An exotherm and the evolution of Hcl gas may be expected when the acylhalide and alcohol are mixed to form the esterification agent. An excess of esterification agent (about 5 to 15 molar equivalents and preferably about 10 molar equivalents) is added to the acid halide intermediate and the reaction proceeds at atmospheric pressure and at a temperature maintained to range from about 0° C. to about the boiling point of the alcohol. When isopropanol is used as the esterifying alcohol, the temperature is preferably maintained to range from about 0° C. to about 80° C., with a temperature of about 75° C. being most preferred. Hcl gas results from the esterification reaction and should be scrubbed during the reaction. The reaction period varies, but yields greater than about 90% are obtained by reacting at about 75° C. for about one to two hours. The resulting esterification product is also of high purity (greater than about 90%), which simplifies product workup and results in improved payloads and cycle times. The resulting benzoic acid ester product can be isolated by removing excess alcohol in vacuo or by precipitating the product. In the former isolation method, the reaction mixture is preferably heated to and maintained at a temperature of about 80° C. to about 90° C. while the alcohol solvent and other volatiles are stripped under reduced pressure. The remaining mixture containing the product is then cooled to ambient temperature. Alternatively, the product may be precipitated by cooling to about 50° C. and adding water, and then isolated by filtering.

In the alternative esterification protocol, the benzoic acid ester of Formula I is prepared by reacting the benzoic acid of Formula If with a trialkylorthoester of Formula F1,

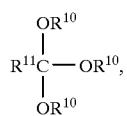

(F1)

wherein in the above formula, $R^{10}$ is $C_{1-5}$ alkyl and $R^{11}$ is hydrogen or alkyl. $R^{10}$ is preferably $C_{3-5}$ alkyl. $R^{11}$ is preferably hydrogen such that the trialkylorthoester is a trialkylorthoformate. Advantageously, trialkylorthoesters such as trialkylorthoformates provide excellent yield of the desired alkyl esters.

The benzoic acid is esterified with the trialkylorthoester in neat or in a suitable solvent. Where solvent systems are used, aromatic hydrocarbon solvents such as toluene, xylene and cymene and relatively high-boiling ethers such as methoxyethylether, diethoxyether or dioxane are suitable solvents. Preferably, the benzoic acid substrate is mixed with excess trialklyorthoester (about 1.1 to about 1.5 molar equivalents with about 1.3 molar equivalents being preferred) and heated to a reaction temperature ranging from about 80° C. to about 150° C., more preferably from about 130° C. to about 140° C., and most preferably at about 135° C. Volatile by-products begin to be driven out of the reaction mixture as the reaction mixture is heated above about 110° C. The reaction is preferably carried out at atmospheric pressure. The reaction time varies depending on the temperature and the concentration of reactants; yields of about 90% are typically obtained using at a temperature of about 135° C. for about 1 to 2 hours. After the reaction, the esterified product may be isolated as a melt by stripping away excess trialkylorthoformate, solvent and volatile by-products, and then cooling. Alternatively, the esterified product may be precipitated by cooling to about 50° C., adding isopropanol and then adding water. The precipitated product is isolated by filtering, optionally rewashing with additional isopropanol/water, and drying.

In a most preferred embodiment, the esterified aryl-pyrazole of Formula II is prepared from the compound of Formula IIf according to the reaction:

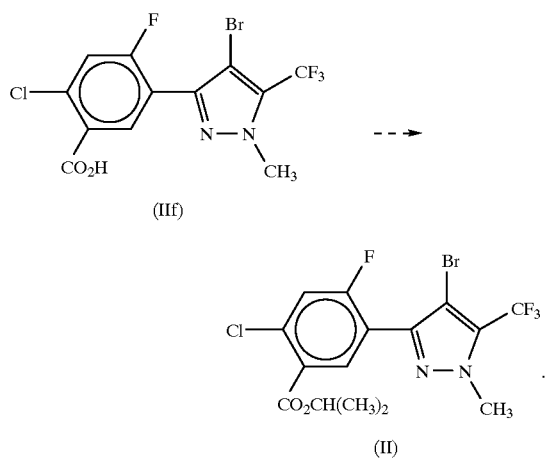

This reaction may be effected substantially as described above using either of the two esterification protocols for preparing compounds of Formula I. Where the first esterification protocol is used, a preferred esterification reagent for preparing the isopropyl ester is formed by mixing about 4% acetyl chloride, by weight, with isopropanol. Where the second esterification protocol is used, the trialkylorthoester esterification reagent is preferably triisopropylorthoformate, where, with reference to Formula F1, $R^{10}$ is isopropanol (—CH(CH$_3$)$_2$) and $R^{11}$ is hydrogen. The formation of the isopropyl ester of Formula II is further exemplified in Example 1 (Processes E-1 and E-2) for the acylhalide/alcohol and trialkylorthoester protocols, respectively.

Order of Process Steps

The process steps for preparing compounds of Formulas I or II are preferably carried out in the order of Processes A–E as presented above: diketone formation (Process A), cyclization (condensation) and alkylation (Process B), oxidation (Process C), halogenation (Process D) and esterification (Process E). However, the exact order is not narrowly critical, and may be varied by persons skilled in the art.

For example, the order of the halogenation step may be varied. Halogenation can be carried out between the alkylation and oxidation steps of the preferred order. With reference to the process steps described above, aryl-pyrazole compounds may be prepared by forming a phenyl diketone from an acetophenone (Process A), condensing the phenyl-diketone and alkylating to form an alkylated pyrazole (Process B), halogenating the pyrazole moiety (Process D), oxidizing the methyl group on the phenyl moiety (Process C) and esterifying (Process E). Compounds of Formula I are prepared according to this embodiment by acylating a compound of Formula Ia (Process A)

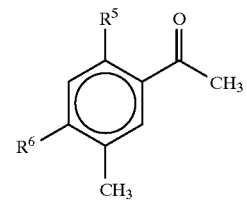

to form a compound of Formula Ib,

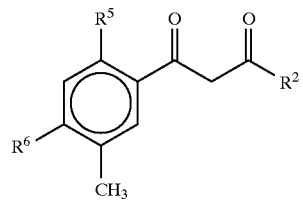

condensing the compound of Formula Ib with hydrazine to form an alkyl-pyrazole-precursor intermediate and alkylating the intermediate (Process B) to form a compound of Formula Id,

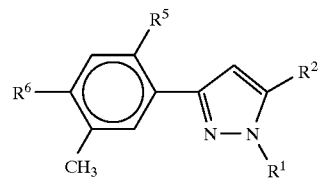

halogenating the compound of Formula Id (Process D) to form a compound of Formula Ig

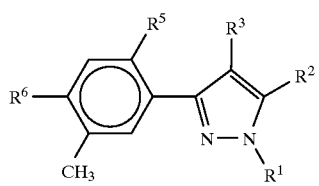
(Ig)

oxidizing the compound of Formula Ig (Process C) to form a compound of Formula If, and

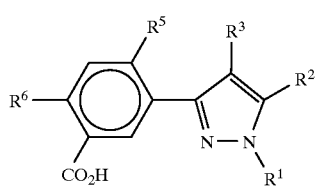
(If)

esterifying the compound of Formula If (Process E) to form a compound of Formula I.

Additionally, the pyrazole moiety could be halogenated after the oxidation and esterification steps. In such a case, the aryl-pyrazoles are prepared by forming a phenyl diketone (Process A), condensing the phenyl-diketone and alkylating to form an alkylated pyrazole (Process B), oxidizing the methyl group on the phenyl moiety to form a benzoic acid pyrazole (Process C), esterifying the benzoic acid (Process E), and halogenating the pyrazole moiety (Process D). Compounds of Formula I are prepared by acylating a compound of Formula Ia (Process A)

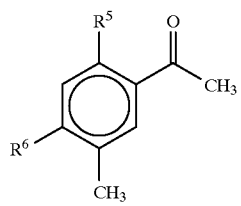
(Ia)

to form a compound of Formula Ib,

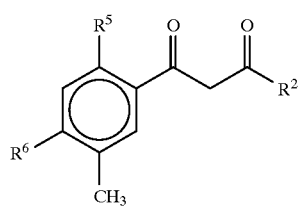
(Ib)

condensing the compound of Formula Ib with hydrazine to form an alkyl-pyrazole-precursor intermediate and alkylating the intermediate (Process B) to form a compound of Formula Id,

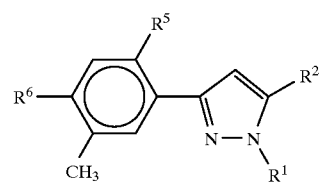
(Id)

oxidizing the compound of Formula Id (Process C) to form a compound of Formula Ie,

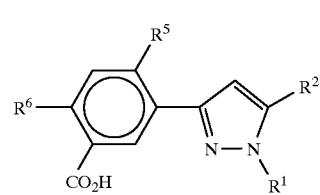
(Ie)

esterifying the compound of Formula Ie (Process E) to form a compound of Formula Ih, and

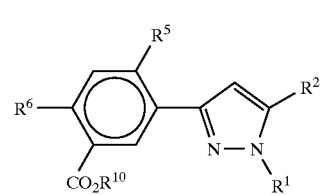
(Ih)

halogenating the compound of Formula Ih (Process D) to form a compound of Formula I.

Another variation to the order of the process steps for preparing aryl-pyrazoles includes oxidizing and esterifying the phenyl moiety before forming the pyrazole. For example, aryl-pyrazoles may be prepared by first oxidizing a methyl-acetophenone to form a carboxylic acid-acetophenone (Process C), esterifying (Process E), forming a phenyl diketone (Process A), condensing the phenyl-diketone and alkylating to form an alkylated pyrazole (Process B) and halogenating the pyrazole moiety (Process D). In particular, compounds of Formula I may be prepared by oxidizing a compound of Formula Ia (Process C)

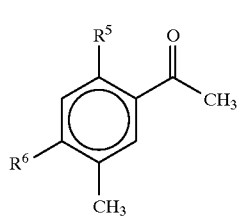
(Ia)

to form a compound of Formula Ii,

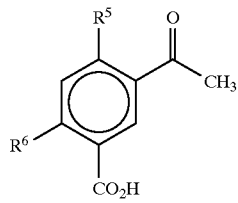

esterifying the compound of Formula Ii (Process E) to form a compound of Formula Ij

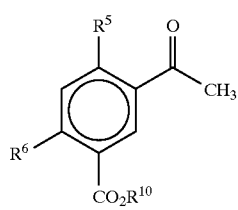

acylating the compound of Formula Ij (Process A) to form a compound of Formula Ik

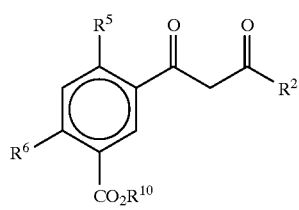

condensing the compound of Formula Ik with hydrazine to form an alkyl-pyrazole-precursor intermediate and alkylating the intermediate (Process B) to form a compound of Formula Ih, and

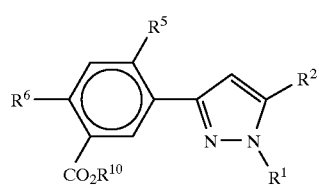

halogenating the compound of Formula Ih (Process D) to form a compound of Formula I.

As another example, an aryl-pyrazole may be prepared by first forming a phenyl-diketone (Process A), oxidizing (Process C) a methyl group on the phenyl moiety of the phenyl-diketone, esterifying (Process E), forming an alkylated pyrazole (Process B) and halogenating (Process D). According to this process, a compound of Formula I may be prepared by acylating a compound of Formula Ia (Process A)

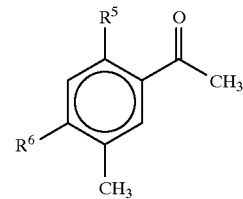

to form a compound of Formula Ib,

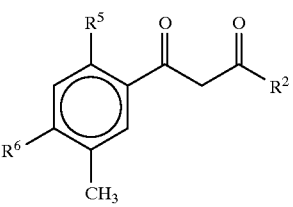

oxidizing the compound of Formula Ib (Process C) to form a compound of Formula Il,

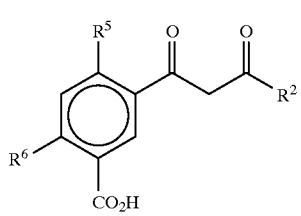

esterifying the compound of Formula Il (Process E) to form a compound of Formula Ik, and

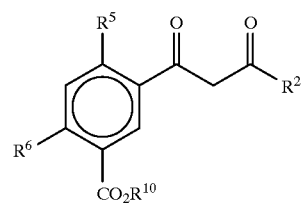

condensing the compound of Formula Ik with hydrazine to form an alkyl-pyrazole-precursor intermediate and alkylating the intermediate (Process B) form a compound of Formula Ih,

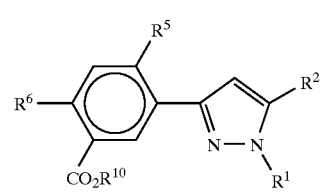

halogenating the compound of Formula Ih (Process D) to form a compound of Formula I.

In still another variation in order, the oxidation step could be carried out before pyrazole formation with the esterification being carried out after pyrazole formation. For example, an aryl-pyrazole may be prepared by first oxidizing a methyl-acetophenone to form a carboxylic acid-acetophenone (Process C), then forming a phenyl diketone (Process A), and condensing the phenyl-diketone and alkylating to form an alkylated pyrazole (Process B), halogenating the pyrazole moiety (Process D) and esterifying (Process E). Specifically, compounds of Formula I may be prepared by oxidizing a compound of Formula Ia Process C)

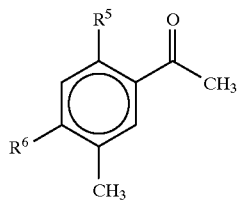

(Ia)

to form a compound of Formula Ii,

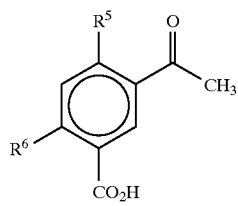

(Ii)

acylating the compound of Formula Ii (Process A) to form a compound of Formula Il

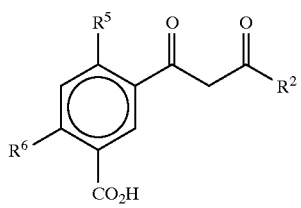

(Il)

condensing the compound of Formula Il with hydrazine to form an alkyl-pyrazole-precursor intermediate and alkylating the intermediate (Process B) to form a compound of Formula Ie,

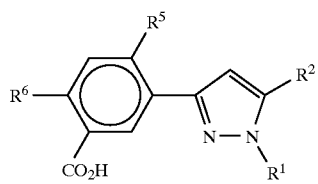

(Ie)

halogenating the compound of Formula Ie (Process D) to form a compound of Formula If, and

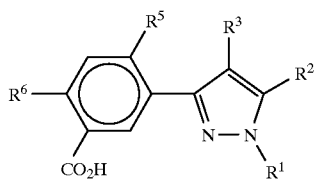

(If)

esterifying the compound of Formula If (Process E) to form a compound of Formula I.

As another example, an aryl-pyrazole may be prepared by first forming a phenyl-diketone (Process A), oxidizing (Process C), forming an alkylated pyrazole (Process B), halogenating (Process D), and esterifying (Process E). 3-aryl-pyrazoles of Formula I may be prepared by acylating a compound of Formula Ia (Process A)

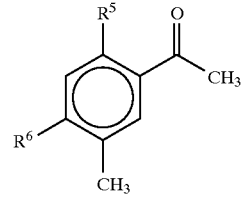

(Ia)

to form a compound of Formula Ib,

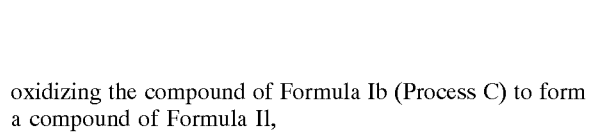

(Ib)

oxidizing the compound of Formula Ib (Process C) to form a compound of Formula Il, (II)

condensing the compound of Formula Il with hydrazine to form an alkyl-pyrazole-precursor intermediate and alkylating the intermediate (Process B) to form a compound of Formula Ie,

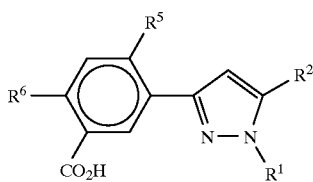

(Ie)

halogenating the compound of Formula Ie (Process D) to form a compound of Formula If, and

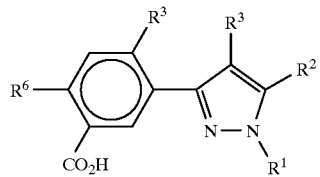

(If)

esterifying the compound of Formula If (Process E) to form a compound of Formula I.

Additionally, the halogenation step could, in these last two examples, be carried out after the esterification. Using this variation, compounds of Formula I may be prepared by acylating a compound of Formula Ia (Process A)

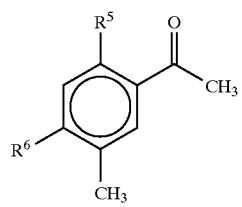

(Ia)

to form a compound of Formula Ib,

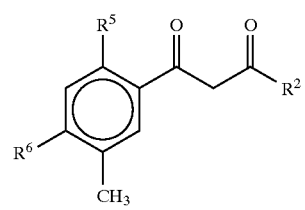

(Ib)

oxidizing the compound of Formula Ib (Process C) to form a compound of Formula Il,

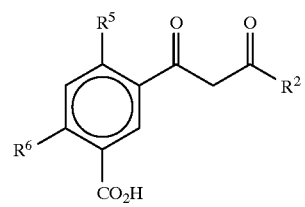

(Il)

condensing the compound of Formula Il with hydrazine to form an alkyl-pyrazole-precursor intermediate and alkylating the intermediate (Process B) to form a compound of Formula Ie,

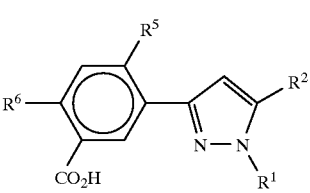

(Ie)

esterifying the compound of Formula Ie (Process E) to form a compound of Formula Ih, and

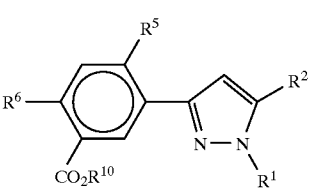

(Ih)

halogenating the compound of Formula Ih (Process D) to form a compound of Formula I.

As another exemplary variation in the preferred order of process steps, aryl-pyrazoles of Formula I may be prepared by oxidizing a compound of Formula Ia (Process C)

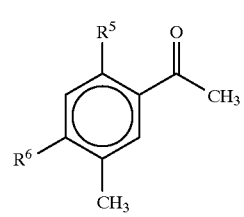

(Ia)

to form a compound of Formula Ii,

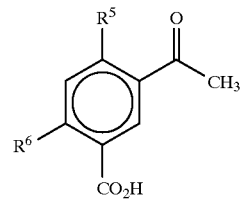

(Ii)

acylating the compound of Formula Ii (Process A) to form a compound of Formula Il

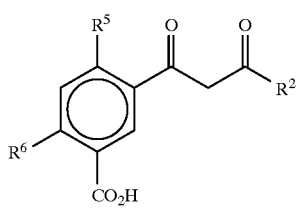

condensing the compound of Formula II with hydrazine to form an alkyl-pyrazole-precursor intermediate and alkylating the intermediate (Process B) to form a compound of Formula Ie,

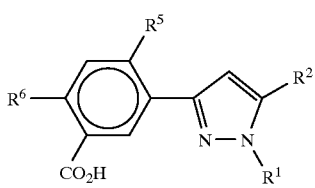

esterifying the compound of Formula Ie (Process E) to form a compound of Formula Ih, and

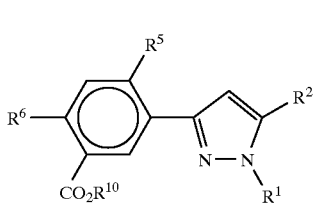

halogenating the compound of Formula Ih (Process D) to form a compound of Formula I. In each of the aforementioned alternative reaction sequences, $R^1$ is $C_{1-5}$ alkyl, $R^2$ is $C_{1-3}$ haloalkyl, $R^3$, $R^5$ and $R^6$ are halogen and $R^{10}$ is $C_{1-5}$ alkyl.

Those skilled in the art will appreciate that yet additional variations in order may be used to prepare aryl-pyrazoles according to the processes of the present invention. The following examples illustrate the principles and advantages of the invention.

EXAMPLES

Example 1

Preparation of isopropyl 5-[4-bromo-1-methyl-5-(trifluoromethyl)-1H-pyrazole-3-yl]-2-chloro-4-fluorobenzoate Process A 1,1,1-trifluoro-4-[4-chloro-2-fluoro-5-methyl-phenyl-1-yl]-2,4-dibutanone (Formula IIb) was prepared from a compound of Formula IIa according to the reaction:

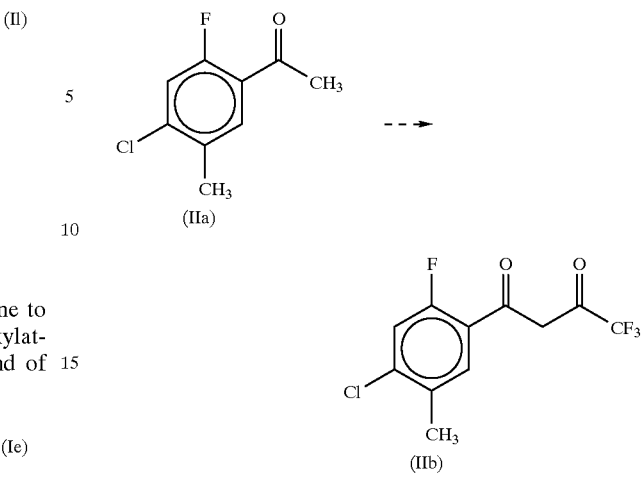

Trifluoroacetyl chloride (2.6 kg, 1.5 molar equiv. relative to the compound of Formula IIa) was bubbled into a solution containing 25% sodium methoxide in methanol (4.24 kg NaMeO, 1.5 molar equiv. relative to the compound of Formula IIa) at −5° C. The addition was controlled so that the temperature did not exceed 40° C., despite the resulting exotherm. Total addition time was about 1.5 hours. The 4-chloro-2-fluoro-5-methyl-acetophenone of Formula IIa (2.434 kg, 13.092 mole) was then added. An additional amount of the sodium methoxide/methanol solution (4.24 kg, 1.5 molar eq.) was added, a mild exotherm was noted, and the reaction mixture was heated to 60° C. and maintained at that temperature for the course of the reaction. The progress of the reaction was monitored by gas chromatography, which indicated completion in about 45 minutes.

In preparation for the cyclization reaction of Process B, the resulting compound of Formula IIb was worked up as follows. A 10% aqueous HCl solution (5.0 kg) was added to neutralize the reaction. The methanol was then stripped at 45–50° C. with a slight vacuum to result in a slurry. Toluene (11.62 kg) was added as a solvent and the aqueous layer was removed. The toluene solution, which contained the product compound of Formula IIb, was washed with DI water (6.63 kg) and used directly in Process B without further processing.

Alternative methods for working up the product compound of Formula IIb were used in additional experiments. In one alternative method, for example, methanol was first stripped at 45–5° C. with a slight vacuum and resulted in a slurry. The temperature was cooled back to ambient temperature and toluene (11.62 kg) was added as solvent. The toluene solution was washed first with a 10% aqueous HCl solution (5.0 kg) and then with DI water (6.63 kg). The aqueous layer was removed and the toluene solution was used in Process B without further processing. In another work-up method, the reaction was first cooled to 50° C., and then neutralized with a 10% aqueous HCl solution (7.0 kg). The solution was further cooled to about 10° C., resulting in a precipitated product. The precipitate was isolated by filtration and then washed with DI water until filtrate pH was greater than about 2. To use the isolated compound in Process B, the isolated precipitate was reslurried in toluene (about 11 kg) without further drying.

Process B 1-methyl-3-[4-chloro-2-fluoro-5-methyl-phenyl-1-yl]-5-trifluoromethyl-pyrazole (Formula IId) was prepared from the compound of Formula IIb according to the reaction:

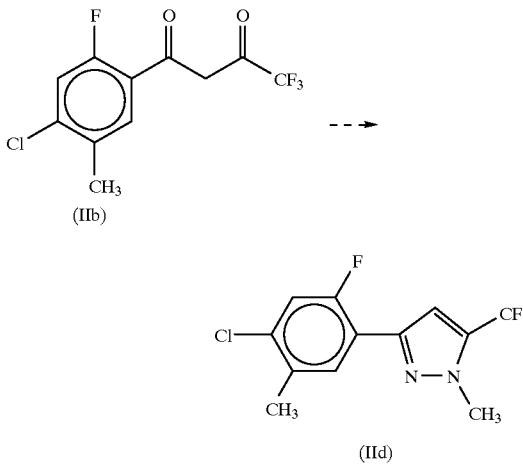

35% aqueous hydrazine (1.1 molar equivalents) was added at ambient temperature to a toluene solution containing 1,1,1-trifluoro-4-[4-chloro-2-fluoro-5-methyl-phenyl-1-yl]-2,4-dibutanone (Formula IIb), prepared as described above. A mild exotherm was noted and the temperature was maintained at about 40° C. throughout the condensation reaction. The reaction mixture was stirred at 40° C. for 30 minutes and reaction progress was monitored by gas chromatography. In some experimental runs, some of the intermediate products precipitated out of solution during the course of the reaction.

Upon completion of the reaction, the reaction mixture was, when necessitated, heated to 70° C. to redissolve precipitated intermediates and/or to facilitate separation of the organic and aqueous phases into distinct layers. The water layer was removed and the toluene solution was washed with a 10% aqueous brine solution (2×2.77 kg). The aqueous brine solution was then removed and discarded.

Dimethylsulfate (1.94 kg, about 1.2 equiv.) was added slowly to the toluene solution containing the alkyl-pyrazole-precursor intermediates, prepared as described above, the speed of addition being controlled so as to minimize large exotherms. After addition of dimethylsulfate, the solution was heated to reflux at 105° C. while azeotroping to remove water. The reaction progress was monitored by gas chromatography. In experimental runs where the reaction did not go to completion, additional dimethyl sulfate (about 150 to 170 grams) was added. After refluxing for about 10 hours, the solution was cooled, washed with an aqueous 10% NaOH solution (5.16 kg), washed with an aqueous 5% NaOH solution (5.16 kg), and then washed with an aqueous 10% brine solution (5.16 kg). Toluene was stripped from the solution and replaced with methanol (2.95 kg). The alkylated pyrazole reaction product was precipitated by adding water (184 grams, 1:16 weight ratio relative to methanol) and then cooling to about 5° C. The precipitated product (about 2.858 kg, light grey solid) was removed by centrifuging. The overall yield for the combined steps of Processes A and B was about 75%.

Process C

5-[1-methyl-5-(trifluoromethyl)-1H-pyrazole-3-yl]-2-chloro-4-fluorobenzoic acid (Formula IIe) was prepared from the compound of Formula IId according to the reaction:

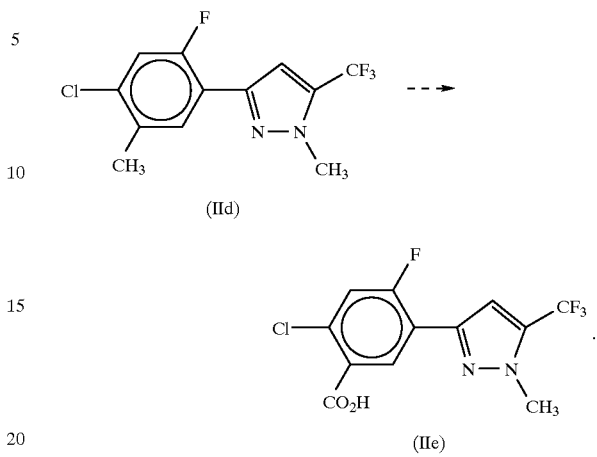

1-methyl-3-[4-chloro-2-fluoro-5-methyl-phenyl-1-yl]-5-trifluoromethyl-pyrazole of Formula IId (2.853 kg, 9.755 moles), prepared as described above, $Co(OAc)_2 \cdot 4H_2O$ (24.16 g, 0.098 mole), $Mn(OAc)_2 \cdot H_2O$ (2.4 g, 0.0097 moles) and NaBr (30.24 g, 0.277 moles) were added to a reactor. Glacial acetic acid (11.00 kg, 184 moles) was then added, followed in succession by the addition of benzoyl peroxide (22.87 g, 0.094 moles—supplied as 32.67 g of a hydrated solid comprising 70% benzoyl peroxide) and acetone (27.66 g, 0.49 moles). Mixing of the substrate, catalysts, promoters and initiator as a reaction mixture was then initiated and continued throughout the reaction. Air at atmospheric pressure was introduced into the reaction mixture. The reaction mixture was heated to about 110° C. and maintained at that temperature throughout the reaction. Reaction progress was monitored using HPLC, and the reaction was typically complete within about 10–20 hours. The reaction mixture containing the product was not isolated or otherwise worked-up, in anticipation of being used in the bromination reaction, described below.

Variations in the aforementioned oxidation experiments were carried out. In experimental runs in which the reaction had been carried out as described above except for the use of hydrogen peroxide instead of benzoyl peroxide, initiation of the oxidation reaction was erratic and sometimes took as long as six hours. In experimental runs in which the reaction had been carried out as described above except that acetone had not been added to the reaction mixture, the time necessary for the reaction to proceed to completion was about 20% to about 30% longer. In further experimental runs using the preferred reaction mixture, oxygen was used in place of air, and independently, elevated pressures were used with both air and oxygen as the purge gas. Moreover, in some experimental runs, the reaction product was isolated by cooling and adding water. The reaction typically resulted in better than about 90% yield of oxidized benzoic acid product at a purity of about 93% to about 97%.

Process D-1

5-[4-bromo-1-methyl-5-(trifluoromethyl)-1H-pyrazole-3-yl]-2-chloro-4-fluorobenzoic acid (Formula IIf) was prepared from the compound of Formula IIe according to the reaction:

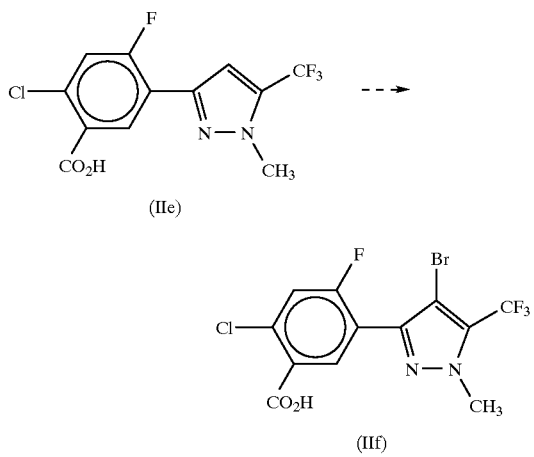

(IIe)

(IIf)

A slurry containing 5-[1-methyl-5-(trifluoromethyl)-1H-pyrazole-3-yl]-2-chloro-4-fluorobenzoic acid in about four parts acetic acid was prepared as described in Process C. Sodium bromide (1.36 kg, 1.35 molar equiv.) was dissolved in deionized water (3.69 kg, about 21 molar equiv.) and slowly added to the acetic acid substrate solution. The addition of NaBr was carried out with aggressive mixing and with care to maintain the temperature above about 70° C. to minimize precipitation in large lumps. $Cl_2$ gas (789 g, 1.15 molar equiv.) was added, resulting in an exotherm. The reaction mass became thicker as the reaction progressed, and the temperature was maintained at about 85° C. to facilitate agitation. Reaction progress was monitored independently by HPLC and fluorine NMR. In cases where the reaction did not proceed to completion, additional chlorine (74 g, 0.1 molar equiv.) was added. The reaction was complete within about 3 hours after the end of chlorine addition.

The reaction mixture was then cooled to ambient temperature and quenched with a 25% aqueous sodium sulfite solution (about 2.8 kg, 0.15 molar equiv.). Additional water (3.69 kg, 20 molar equivalents) was added to aid mixing and to fully precipitate the brominated product. After waiting about 30 minutes, the product was isolated by filtration, washed with DI water, and thoroughly dried in preparation for subsequent use in Process E. Approximately 3.50 kg of brominated aryl-pyrazole product (Formula IIf) was isolated having a purity of between about 93–97% and resulting in a yield of about 80% to about 90% relative to the alkylated pyrazole compound of Formula IId.

Process D-2

The bromination was performed as described above (Process D-1) except sodium hypochlorite was used instead of chlorine gas as the oxiding agent. After sodium bromide (1.36 kg, 1.35 molar equiv.) was dissolved in deionized water (3.69 kg, about 21 molar equiv.) and added to the slurry containing 5-[1-methyl-5-(trifluoromethyl)-1H-pyrazole-3-yl]-2-chloro-4-fluorobenzoic acid in acetic acid, an aqueous NaOCl solution (1.5–2.4 molar equiv.) was added slowly while stirring and while maintaining the temperature at 70° C. Reaction progress was monitored by HPLC and the reaction was complete within about 3 hours after the addition of NaOCl. After completion of reaction, the solution was cooled and quenched with sodium sulfite as described above. The product was isolated as described above with similar yields.

Process E-1

Isopropyl 5-[4-bromo-1-methyl-5-(trifluoromethyl)-1H-pyrazole-3-yl]-2-chloro-4-fluorobenzoate (Formula II) was prepared from the compound of Formula IIf according to the reaction

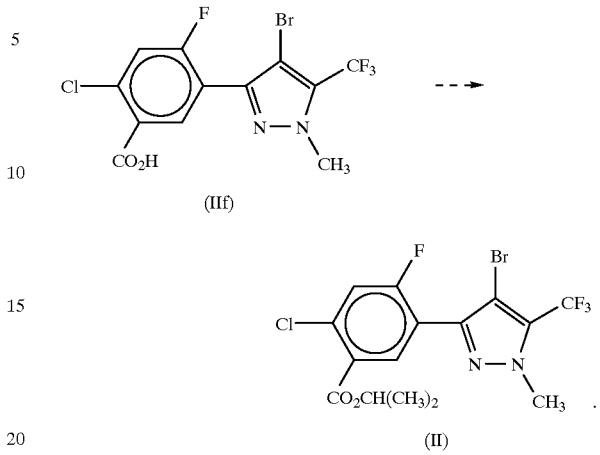

(IIf)

(II)

5-[4-bromo-1-methyl-5-(trifluoromethyl)-1H-pyrazole-3-yl]-2-chloro-4-fluorobenzoic acid (3.50 kg) prepared as described above and thoroughly dried was dissolved in toluene (7.38 kg, 9 molar equiv.) at ambient temperature. Thionyl chloride (1.58 kg, 1.5 molar equiv.) and dimethyl formamide (9.2 g, 0.01 molar equiv.) were added thereto at 25° C., and the reaction mixture was slowly heated to 75° C. The heating rate was controlled so as to minimize foaming of the solution. The reaction progressed at 75° C. and was complete within about 2 hours. The toluene solvent and excess thionyl chloride were stripped in vacuo while maintaining the temperature at 75° C., leaving the corresponding acid chloride intermediate (about 3.8 kg) as an oil.

Reagent grade isopropanol (5.53 kg, 10.6 molar equiv.) was mixed with acetyl chloride (221 g) to form an esterification agent. An exotherm and evolution of HCl gas was observed. The esterification agent was added to the acid chloride intermediate at 75° C. The reaction mixture was stirred and maintained at a temperature of 75° C. during the reaction, and HCl off gas was scrubbed. Reaction progress was monitored by gas chromatography and was complete within about 2 hours.

The reaction mixture was then cooled to about 50° C. Water (11 kg) was slowly added to precipitate the product. The product was isolated by filtration, resulting in a tan to white waxy solid with a purity of greater than about 92% and a yield of about 90% to about 94%.

In other experiments, an alternative method for product work-up included stripping the product mixture under reduced pressure and at temperatures ranging from about 80° C. to about 90° C. to remove solvent and all volatiles. The melt was then cooled to ambient temperatures to form a brick-like solid.

Process E-2

In an alternative esterification protocol, 5-[4-bromo-1-methyl-5-(trifluoromethyl)-1H-pyrazole-3-yl]-2-chloro-4-fluorobenzoic acid (300 g, 0.747 moles), prepared as described above, was mixed with triisopropylorthoformate (186 g, 1.3 molar equiv.) and then heated to about 135° C. to about 140° C. with removal of the low-boiling by-product. The reaction was monitored by HPLC and was completed within about 1.5 hours.

Excess triisopropylorthoformate and volatile by-products were stripped at reduced pressure, and the resulting oil was cooled and isolated as a melt. In other experiments, the product was precipitated by cooling the reaction mixture to about 50° C., adding isopropanol (480 g), and subsequently adding water (600 g). The precipitated product was further washed with a water/isopropanol solution (240 g, 1:0.8 ratio of water:isopropanol, by weight). The product was isolated by filtration, and dried. Product purity was greater than about 92 percent and yield was about 90%.

Example 2

Preparation of 3(5)-[4-chloro-2-fluoro-5-methylphenyl-1-yl]-5(3)-(trifluoromethyl)-1H-pyrazole 3(5)-[4-chloro-2-fluoro-5-methylphenyl-1-yl]-5(3)-(trifluoromethyl)-pyrazole, structurally represented as the compound of Formula IIc,

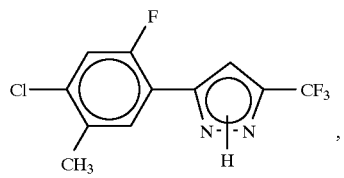

(IIc)

was prepared from 1,1,1-trifluoro-4-[2-chloro-4-fluoro-5-methylphenyl-1-yl]-2,4-dibutanone. The dibutanone (20.6 g) was dissolved in 100 ml of acetic acid in a 500 ml flask equipped with a magnetic stirrer. Hydrazine (2.85 g) was added all at once and an exotherm to 45° C. was observed. The solution was heated to 110° C. and maintained at that temperature for 15 minutes. The reaction mixture was then cooled to room temperature and poured into water (200 ml), resulting in a white solid precipitate. The precipitated product was isolated by filtering, and then air dried overnight. The solid was washed with 200 ml of hexanes and air dried briefly to afford the aryl-pyrazole compound of Formula IIc (19.6 g) as a white solid (m.p. 159–160° C.; Anal. Calcd. for $C_{11}H_7N_2F_4Cl_1$: C-47.42, H-2.53, N-10.05; Found: C-47.36, H-2.58, N-10.07). Product yield was about 97%.

Example 3

Regioselective N-alkylation of 3(5)-aryl-5(3)-haloalkyl-pyrazoles

The preparation of regiospecific alkylated-pyrazoles of Formula IIIe,

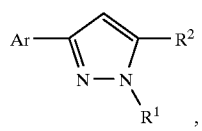

(IIIe)

were prepared from phenyl-diketones of Formula IIIb according to the reaction

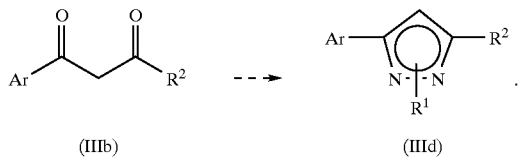

wherein in the above formulae, Ar is 2,5-difluorophenyl and $R^2$ is $CF_3$. The compounds of Formula IIIb were cyclized with hydrazine, and the resulting intermediate(s) alkylated with a variety of methylating agents, $CH_3X$, under different solvent and reaction conditions. The ratio percent of the resulting 3-aryl and 5-aryl isomers for each of the several runs is shown in Table 3-1.

TABLE 3-1

| Alkylating agent | Conditions (solvent, temperature) | % N-methyl products | |
|---|---|---|---|
| | | 3-Aryl | 5-Aryl |
| $CH_3I$ | acetone, $K_2CO_3$, RT | 70 | 30 |
| $CH_3I$ | DMF, $K_2CO_3$, RT | 70 | 30 |
| $CH_3I$ | DMSO, $K_2CO_3$, RT | 65 | 35 |
| $(CH_3)_2SO_4$ | 50% $NaOH/CH_2Cl_2$, RT | 64 | 36 |
| $CH_3BR$ | acetone, $K_2CO_3$, RT | 78 | 24 |
| $(CH_3)_2SO_4$ | acetone, $K_2CO_3$, RT | 77 | 23 |
| $CH_3BR$ | acetone, $K_2CO_3$, 0° C. | 80 | 20 |
| $(CH_3)_2SO_4$ | toluene, reflux | 96 | 4 |
| $(CH_3)_2SO_4$ | toluene, $K_2CO_3$, RT | 55 | 45 |

When the reaction was carried out under basic conditions using potassium carbonate or sodium hydroxide as a base, the percent of 3-aryl isomer selectively formed over the 5-aryl isomer ranged from about 55% to about 80% of the total N-methyl pyrazoles products prepared, with the better selectivity being obtained using less reactive methylating agents, such as methyl bromide, and lower temperatures. However, significantly improved selectivity resulted by running the reaction under acidic conditions. Using a dimethylsulfate methylating agent in refluxing toluene (forming methyl-sulfonic acid as the reaction proceeds), about 96% of the alkylated aryl-pyrazole product was the desired 3-aryl isomer. High-selectivity of the 3-aryl isomer was similarly obtained when the reaction was repeated under acidic conditions, and when the same reaction conditions (dimethylsulfate in refluxing anhydrous toluene were used with different substituents on the phenyl group, as shown in Table 3-2.

TABLE 3-2

| Ar | % N-methyl products | |
|---|---|---|
| | 3-Aryl | 5-Aryl |
| 2,5-difluoro-phenyl | 96 | 4 |
| 2,4-difluoro-phenyl | 96 | 4 |
| 2,4-dichloro-phenyl | 88 | 12 |
| 4-chloro-2-fluoro-5-methyl-phenyl | 91 | 9 |

In each of the aforementioned reactions, the regiochemical assignment of the alkylated haloalkyl pyrazoles was determined by comparison of the $^{13}C$ nmr chemical shifts of the 3 and 5 carbons of the pyrazole rings. Briefly, for the aryl substituent, the C3 carbon of the 3-aryl isomer has greater hydrazone character and appears at about 143 ppm, whereas the C5 carbon of the 5-aryl isomer has greater enehydrazine character and appears upfield at about 133 ppm. These assignments are consistent with the results of long-range coupling experiments and with an X-ray structure obtained for one 3-aryl isomer.

Example 4

Preparation of 3(5)-aryl-5(3)-difluorochloromethyl-pyrazole; decomposition of the same while alkylating under basic conditions and successful alkylation of the same under acidic conditions A 3-aryl-5-haloalkyl-pyrazole of Formula IIIc,

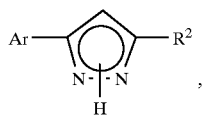
(IIIc)

wherein Ar was 4-chlorophenyl and $R^2$ was $CF_2Cl$ was prepared from 1,1-difluoro-1-chloro-4-[4-chlorophenyl-1-yl]-2,4-dibutanone. A solution of the dibutanone (60.0 g, 0.240 moles) in glacial acetic acid (250 ml) was stirred and treated at once with hydrazine (0.253 moles, 8 ml). A small temperature increase was observed. The mixture was refluxed for one hour, allowed to cool, and added to water (500 ml). The product was extracted with ether, combined extracts were washed with water followed by a 10% sodium bicarbonate solution and concentrated in vacuo to yield the aryl-pyrazole compound of Formula IIIc.

The aryl-pyrazole of Formula IIIc was alkylated under basic conditions ($K_2CO_3$, MeI). However, the basic alkylation resulted in decomposition without any alkylated pyrazole products being formed. The incompatibility of the $CF_2Cl$ group with base was confirmed by treatment of the intermediate (Formula IIIc) with carbonate in the absence of an alkylating agent. In this case, decomposition occurred in less than one hour at room temperature.

However, alkylation of an analogous 3-aryl-5-haloalkyl-pyrazole (with Ar as 4-chloro-2-fluoro)-5-methoxy-phenyl and $R^2$ as $CF_2Cl$) was successful under acidic conditions. 5-[4-chloro-2-fluoro-5-methoxy-phenyl-1-yl]-3-(chlorodifluoromethyl)-pyrazole (14.50 g, 0.0466 moles) in toluene was refluxed in a dean-stark trap for one hour, but no water was collected. Dimethyl sulfate (5.61 g, 0.0445 moles) was added via syringe and the reaction mixture was refluxed for 3.5 hours. The product mixture was washed with equal volume of NaOH (2.5N), and the organic layer was filtered. The solvent was removed in vacuo and the resulting product was recrystallized four times in succession from hexanes to result in an alkylated aryl-pyrazole (9.22 g, 73% yield) of white crystalline solid (m.p. 73–74° C.; Anal. Calcd. for $C_{12}H_9N_2OF_3Cl_2$: C-44.33, H-2.79, N-8.62; Found: C-44.32, H-2.77, N-8.60).

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A process for preparing a compound of Formula IIId,

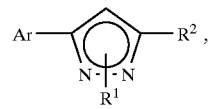
(IIId)

comprising condensing a phenyl-diketone of Formula IIIb

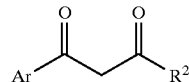
(IIIb)

with hydrazine in a reaction mixture comprising a solvent for said phenyl-diketone to form an alkyl-pyrazole-precursor intermediate, hydrazine being present in the reaction mixture in a stoichiometric excess amount relative to the phenyl-diketone, the amount of excess hydrazine being at least about 15 mole percent of a reference amount, the reference amount being the sum of the molar amount of unreacted phenyl-diketone and the molar amount of intermediate formed, removing the excess hydrazine from the reaction mixture leaving said intermediate in said solvent, and without recovering said intermediate from said solvent alkylating the intermediate with an alkylating agent, wherein: Ar is phenyl or substituted phenyl; $R^1$ is alkyl or alkyl substituted with halogen, amino, nitro, cyano, hydroxy, carboxy, alkoxy, thio, mercaptoalkyl or alkylthio; and $R^2$ is alkyl, hydroxy, alkoxy, acyl, carboxylic acid and aldehyde, amide and ester derivatives thereof, halogen, haloalkyl, amino, nitro, cyano, mercaptoalkyl, alkylthio, alkylsulfinyl, alkylsulfonyl, alkylphosphinyl or alkylphosphonyl.

2. The process as set forth in claim 1 wherein $R^1$ is $C_{1-5}$ alkyl and $R^2$ is $C_{1-3}$ haloalkyl.

3. The process as set forth in claim 1 wherein Ar is of the Formula Ar-2

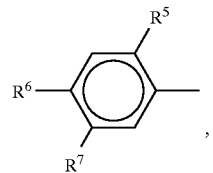
(Ar-2)

wherein: $R^5$ and $R^6$ are halogen and $R^7$ is lower alkyl, haloalkyl, or

where W is hydrogen, hydroxy, halogen, or —$OC_{1-5}$ alkyl.

4. The process as set forth in claim 3 wherein $R^1$ is $C_{1-5}$ alkyl, $R^2$ is $C_{1-3}$ haloalkyl, and $R^7$ is lower alkyl.

5. The process as set forth in claim 3 wherein $R^1$ is methyl, $R^2$ is trifluoromethyl, $R^5$ is fluoro, $R^6$ is chloro and $R^7$ is methyl.

6. The process as set forth in claim 1 wherein the amount of excess hydrazine ranges from about 15% to about 25% of the reference amount.

7. A process for preparing a compound of Formula IIId,

(IIId)

comprising condensing a phenyl-diketone of Formula IIIb

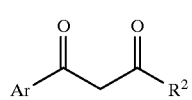
(IIIb)

with hydrazine in a reaction mixture comprising an organic solvent for said phenyl-diketone and water as a solvent for said hydrazine to form an alkyl-pyrazole-precursor intermediate, the reaction mixture having an organic phase and an aqueous phase, hydrazine being present in the reaction mixture in a stoichiometric excess amount relative to the phenyl-diketone, removing excess hydrazine from the reaction mixture by removing the aqueous phase from the reaction mixture leaving said intermediate in said solvent, and without recovering said intermediate from said solvent alkylating the intermediate with an alkylating agent, wherein: Ar is phenyl or substituted phenyl; $R^1$ is alkyl or alkyl substituted with halogen, amino, nitro, cyano, hydroxy, carboxy, alkoxy, thio, mercaptoalkyl or alkylthio; and $R^2$ is alkyl, hydroxy, alkoxy, acyl, carboxylic acid and aldehyde, amide and ester derivatives thereof, halogen, haloalkyl, amino, nitro, cyano, mercaptoalkyl, alkylthio, alkylsulfinyl, alkylsulfonyl, alkylphosphinyl or alkylphosphonyl.

8. The process as set forth in claim 7 wherein $R^1$ is $C_{1-5}$ alkyl and $R^2$ is $C_{1-3}$ haloalkyl.

9. The process as set forth in claim 7 wherein Ar is of the Formula Ar-2

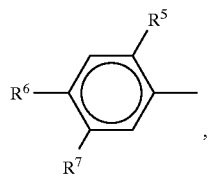
(Ar-2)

wherein: $R^5$ and $R^6$ are halogen and $R^7$ is lower alkyl, haloalkyl, or

where W is hydrogen, hydroxy, halogen, or $—OC_{1-5}$ alkyl.

10. The process as set forth in claim 9 wherein $R^1$ is $C_{1-5}$ alkyl, $R^2$ is $C_{1-3}$ haloalkyl and $R^7$ is lower alkyl.

11. The process as set forth in claim 9 wherein $R^1$ is methyl, $R^2$ is trifluoromethyl, $R^5$ is fluoro, $R^6$ is chloro and $R^7$ is methyl.

12. The process as set forth in claim 7 wherein the reaction mixture is a single phase and excess hydrazine is removed from the reaction mixture by liquid-liquid extraction.

13. The process as set forth in claim 7 wherein excess hydrazine is removed from the reaction mixture by heating the reaction mixture to redissolve into the organic phase any amount of precipitate which may have formed and to separate the aqueous phase from the organic phase, and removing the aqueous phase from the reaction mixture.

14. The process as set forth in claim 7 wherein the amount of excess hydrazine in the reaction mixture is at least about 15 mole percent of a reference amount, the reference amount being the sum of the molar amount of unreacted phenyl-diketone and the molar amount of intermediate formed.

* * * * *

UNITED STATES PATENT AND TRADEMARK OFFICE
CERTIFICATE OF CORRECTION

PATENT NO.: 5,969,153
DATED: 10/19/99
INVENTOR(S): Hamper et al.

It is certified that errors appear in the above-identified patent, and that said Letters Patent is hereby corrected as shown below.

Column 52, Claim 12, line 26, delete "7" and insert --1--

Signed and Sealed this

Ninth Day of May, 2000

Attest:

Q. TODD DICKINSON

Attesting Officer     Director of Patents and Trademarks